United States Patent
Lin et al.

(10) Patent No.: US 7,348,032 B2
(45) Date of Patent: Mar. 25, 2008

(54) **METHOD FOR EXTRACTING ANTINEOPLASTIC COMPONENTS FROM *BUPLEURUM SCORZONERIFOLIUM***

(75) Inventors: Shinn-Zong Lin, Taipei (TW); Horng-Jyh Harn, Taipei (TW)

(73) Assignee: Buddhist Tzu Chi General Hospital, Hualien (TW)

( * ) Notice: Subject to any disclaimer, the term of this patent is extended or adjusted under 35 U.S.C. 154(b) by 366 days.

(21) Appl. No.: 10/690,992

(22) Filed: Oct. 21, 2003

(65) Prior Publication Data

US 2005/0013879 A1    Jan. 20, 2005

(30) Foreign Application Priority Data

Jul. 16, 2003    (TW) ............... 92119380 A

(51) Int. Cl.
*A61K 36/00*    (2006.01)
*A61K 9/00*    (2006.01)

(52) U.S. Cl. ..................... 424/725; 424/400

(58) Field of Classification Search ............ 424/725
See application file for complete search history.

*Primary Examiner*—Christopher R Tate
*Assistant Examiner*—Randall Winston
(74) *Attorney, Agent, or Firm*—Edwards, Angell, Palmer & Dodge, LLP; Peter F. Corless; Dwight D. Kim

(57) ABSTRACT

A method for extracting antineoplastic component from *Bupleurum scorzonerifolium* applicable in treating cell proliferative disorder is proposed. The antineoplastic components of *Bupleurum scorzonerifolium* include at least a Y-butyolactone centred heterocyclic compound with a Z configuration or E configuration at its carbon 2(5) position, and molecules, such as Chaihulactone, Isochaihulactone, Chaihulactone analogues or derivatives containing in the heterocyclic compound. From results of cell and molecular biological studies, in vivo animal test, and histological study, it is found that antineoplastic components extracted from *Bupleurum scorzonerifolium* are effective in suppressing a variety of cancer cell growths, inhibiting telomerase activity, as well as effective in killing with high specificity Taxol-resistant tumor cells at later stage of chemical therapy, making the components a new choice for anti-cancer agent, anti-HIV agent, or synergistic agent.

19 Claims, 26 Drawing Sheets

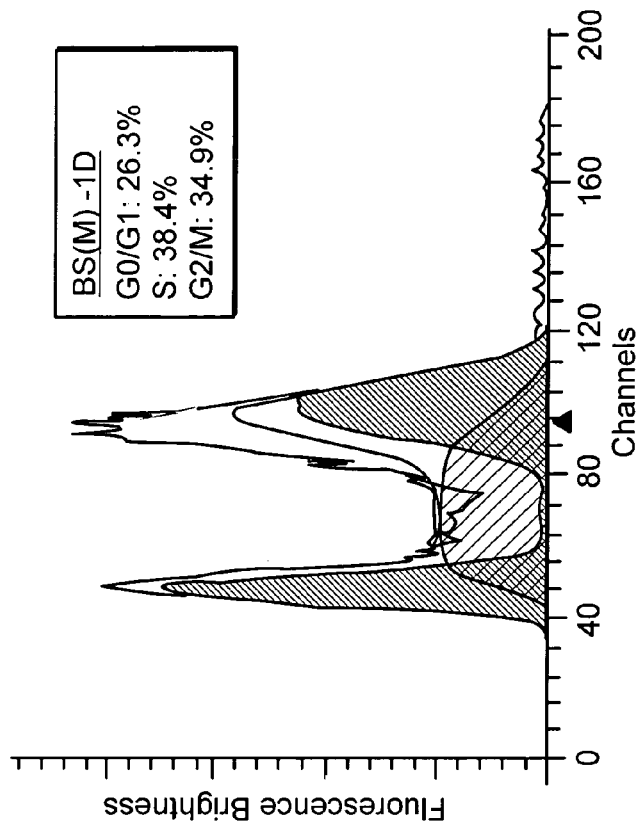
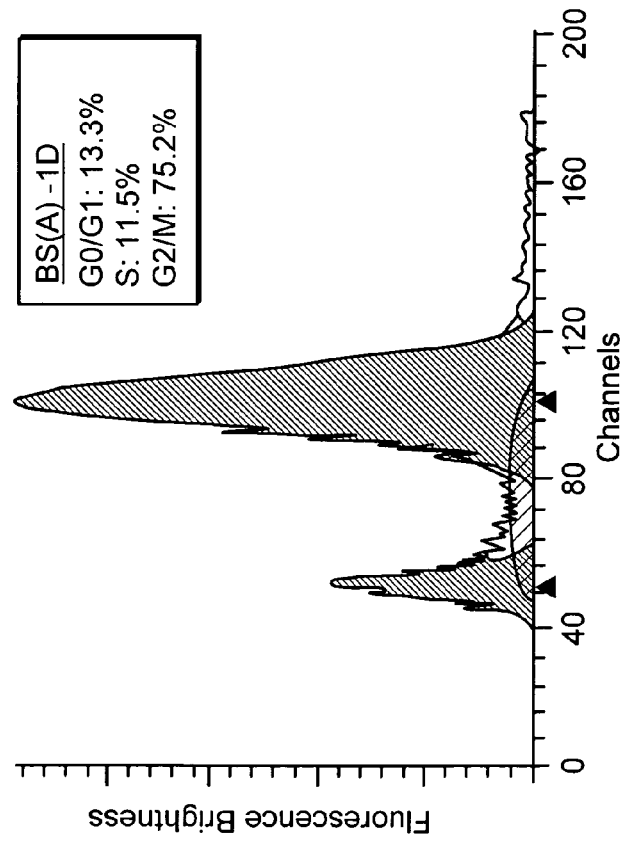
FIG. 2A
FIG. 2B

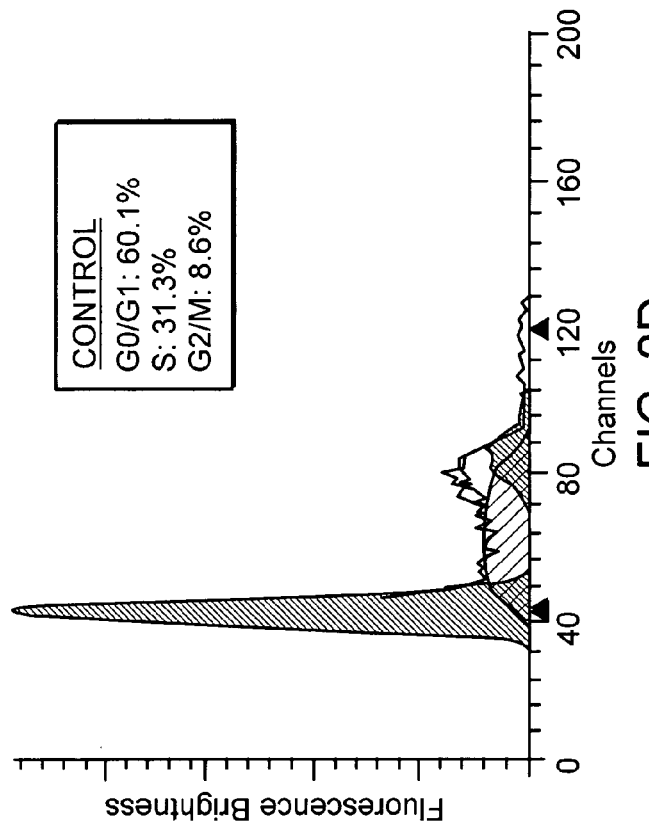
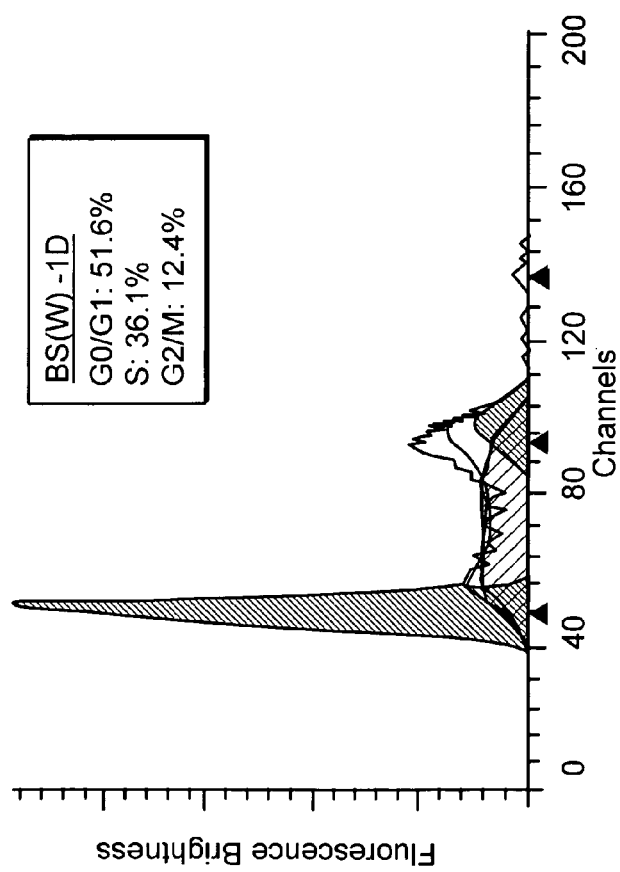

(300mg/kg of BS-AE)

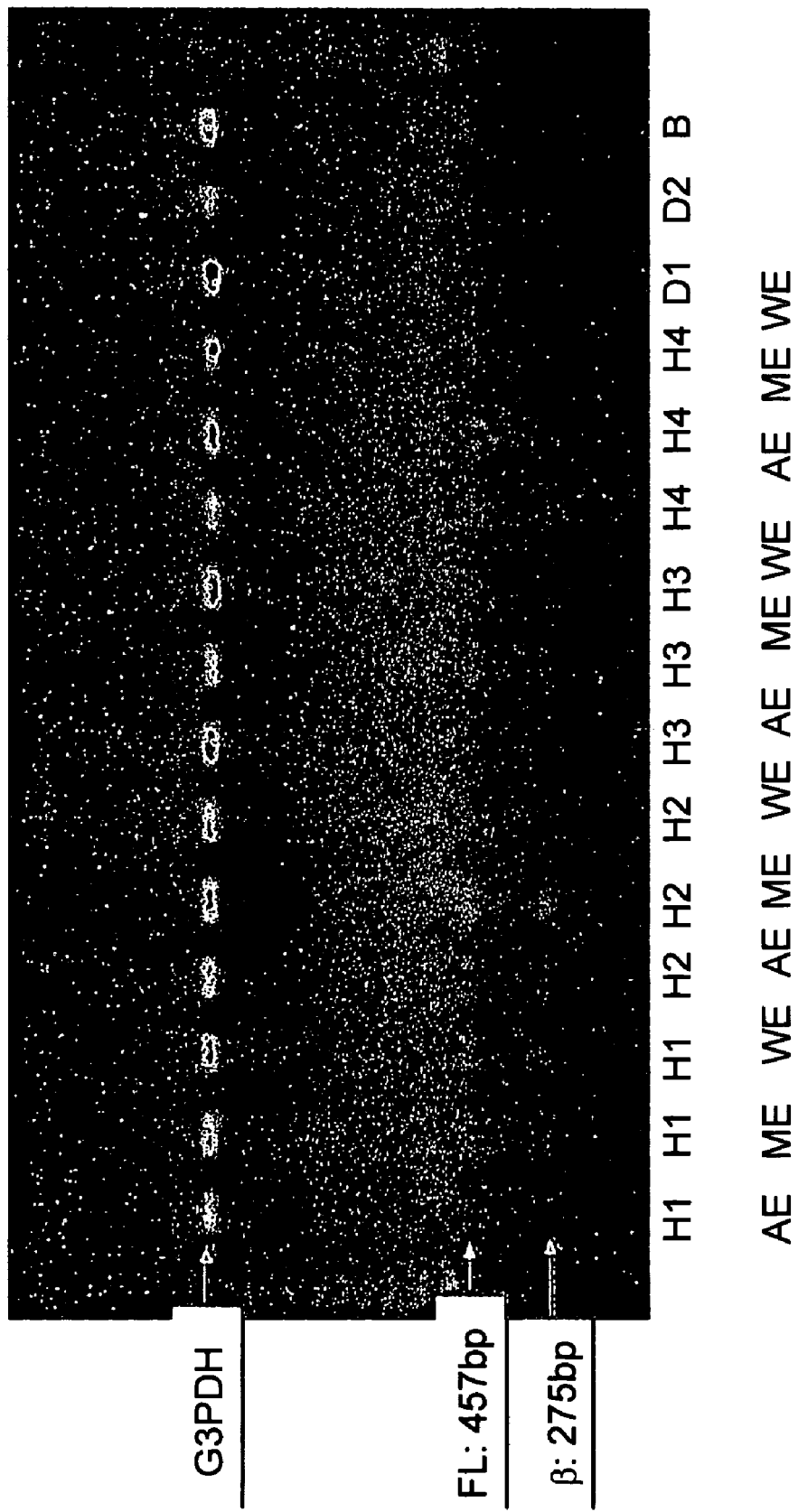

METHOD FOR EXTRACTING ANTINEOPLASTIC COMPONENTS FROM BUPLEURUM SCORZONERIFOLIUM

FIELD OF THE INVENTION

The present invention relates to a method for extracting antineoplastic components. More specifically, this invention relates to a method for extracting from *Bupleurum scorzonerifolium* antineoplastic components containing Y-butyolactone centred heterocyclic compounds that are potentially effective in treating tumors such as hepatoma, lung cancer, ovarian cancer, human malignant glioblastoma and colorectal cancer.

BACKGROUND OF THE INVENTION

Cancer, a cell proliferative disorder, is the leading cause of death worldwide. In 1993, Boring et al. estimated approximately 526,000 deaths from cancer alone in the U.S. each year. For example, breast cancer has been the leading cause of death from cancer in woman between the age of 40 and 55. And with increasing pollutions, the incidence of developing ovarian carcinoma, lung cancer, liver cancer and skin cancer has also increased. Studies from Fitzpatrick et al. in 1986 indicated the number of cancer occurrence has increased six times since 1945, revealing the urgent need for a novel method in diagnosis and treatment for cancer.

It was found from the current cancer studies that the senescence, replication and division of eukaryocyte are all regulated by the cell cycle. During a cell replication, chromosome numbers and deoxyribonucleic acid (DNA) content of the cell increased from 2N to 4N in order to produce two daughter cells after cell mitosis, so that each daughter cell has 2N chromosomes. In 1995, Blackburn et al. discovered a repeat sequence at the end of each chromosome, (5'TTAGGG), which is now known as a telomere is shortened after each mitotic cycle. And when the telomere shortens to a critical length, the telomere that covers the terminal end of the chromosome becomes sticky and causes abnormal pairing of the chromosomes and even a cell death in some cases.

In 1995, Feng et al. discovered a high expression of a ribonucleoprotein complex called telomerase that binds on the telomere at the end of the chromosome from the genetic studies of germ-line cells, stem cells, and tumor cells. The role of this telomerase is to maintain the telomere length, preventing the telomere to become shortened after multiple mitosis. The presence of telomerase helps the cell to escape from the cell cycle and become immortal.

Further research on telomerase activity using Telomerase Repeat Amplification Protocol (TRAP), lead to the finding of significant high telomerase activity in tumor cells and in germ cells, whereas almost no telomerase activity is found in normal somatic cells. In 1994 and 1995, Kim and Broccoli et al have also demonstrated an important role of telomerase in controlling apoptotic cascade of tumor cells. Thus, telomerase activity and its expression level are useful in cancer diagnosis and prognosis during cancer treatment due to its high specificity.

It has been proven from past research works that human immunodeficiency virus (HIV) causing acquired immune deficiency syndrome (AIDS) is a (ribonucleic acid) RNA virus that replicates by reverse transcription in the host cell. The viral replication is known to be regulated by reverse transcriptase that transcribes viral RNA as a piece of DNA inserted into the host DNA for replication. With many years of clinical research, Azidothymidine (AZT), a derivative of thymidine has been developed to treat HIV patients by inhibiting the enzyme activity of the reverse transcriptase, particularly by down regulating expression of human telomerase reverse transcriptase (hTERT). However, there are still limitations for AZT in terms of its inhibitory effect on viral replication of HIV.

On the other hand, from many years of clinical experiences in Chinese medicine, it was found that many Chinese herbs contain potent anti-cancer chemical components. Among these, several Chinese plants such as *Camptotheca acuminata* (camptothecin) and *Cephalotaxus* sp. (homoharringtonine/harringtonine) have proved to be very effective in cancer treatment after selection using TRAP assay. Moreover, in comparison with current anti-cancer drugs, those Chinese herbs have shown less side effects, like reduction in number of white cells, cachexia and so on. Thus, extraction of anti-cancer components from Chinese herbs opens up a new window for quality control of herbal extracts or prescription and developing a novel anti-cancer agent or anti-HIV agent in the future.

For example, paclitaxel (commercially known as TAXOL) having a diterpene core, is isolated from the Pacific yew tree and widely used as a potent chemotherapeutic agent to treat a variety of solid cancers. Paclitaxel has a molecular formula of $C_{47}H_{51}NO_{14}$, molecular weight of 854 Da.

Paclitaxel is mainly used in treating ovarian cancer, breast cancer metastasis, lung cancer and melanoma via its cytotoxicity. This chemical is a mitotic spindle poison that inhibits depolymerization of tubulin by combining to β-tubulin of cell cytoskeleton, so as to interrupt cell mitosis and initiate cell death for the tumor cell. Therefore, Taxol is effective in delivering toxicity towards tumor cells at the initial treatment stage, improving the survival rate of the patient by about 15% in two years.

However, as the treatment was prolonged, many tumor cells gradually developed drug resistant to Taxol. From the recent research, it was discovered that some of Taxol resistant cells exhibit different β-tublin expression level and different electrophoresis mobility from the conventional tumor cells. Research works from Horwitz et al. in 1997 have shown that tumor cells (for example human lung tumor cell lines A549-T12 and A549-T24) are capable of changing their configuration of six P-tubulin subunits to prevent binding with paclitaxel. Instead, paclitaxel is discharged out of the cell through ion pumping, making the tumor cells drug-resistant to paclitaxel after a period of chemotherapy.

Also, other anti-cancer agents such as 5-fluorouracil, epothilone, cisdiammine dichloroplatinum (Cisplatin), procarbazine and cyclophosphamide when clinically used alone or in conjunction with paclitaxel cannot provide a satisfactory outcome in terms of killing the cancer cells developed with drug resistant to paclitaxel. Results from cell culture experiment also indicate that it is difficult to effectively inhibit proliferation of Taxol-resistant tumor cells using current anti-cancer drugs. In order to achieve a higher efficacy, it is often necessary to increase the administering dosage. For example, in an animal experiment, a rat may be injected with 300 mg/kg of paclitaxel. However this would result in high degree of necrosis for the normal cells due to its strong cytotoxicity possessed by the drug.

Thus, in order to improve the cytotoxic effect towards tumor cells at latter stages of chemotherapy, it is imperative to find and isolate anti-cancer components from Chinese herbs that have previously shown promising result in the treatment of cancer to effectively suppress proliferation of Taxol-resistant tumor cell lines.

SUMMARY OF THE INVENTION

A primary objective of the present invention is to provide a method for extracting antineoplastic components from *Bupleurum scorzonerifolium*, which components contain Y-butyrolactone centred heterocyclic compounds or salts, esters and ketones, such as isochaihulactone, chaihulactone, and chaihulactone that are pharmacologically compatible to effectively inhibit proliferation of Taxol-resistant tumor cells.

Another objective of the present invention is to provide a method for extracting Y-butyrolactone centred heterocyclic compounds or salts, esters, ketones that are pharmacologically compatible from *Bupleurum scorzonerifolium* to effectively inhibit proliferation of human hepatoma, ovarian cancer, lung cancer, malignant glioblastoma or colorectal carcinoma.

A further objective of the present invention is to provide a method for extracting Y-butyrolactone centred heterocyclic compounds or salts, esters, ketones that are pharmacologically compatible from *Bupleurum scorzonerifolium* to effectively inhibit telomerase activity.

One other objective of the present invention is to provide a method for extracting from *Bupleurum scorzonerifolium* extracts anti-neoplastic components having a synergistic effect on the currently available anti-tumor drug to achieve a higher efficacy in treating human hepatoma, ovarian cancer, lung cancer, malignant glioblastoma or colorectal carcinoma.

In order to achieve the foregoing and other objectives, the method for extracting antineoplastic components from *Bupleurum scorzonerifolium* proposed by the present invention comprises extracting *Bupleurum scorzonerifolium* extracts for treating cancer cells of lung cancer, ovarian cancer hepatoma, malignant glioblastoma and colorectal carcinoma. The present invention further comprises isolation of individual antineoplastic components or pharmacologically compatible salts, esters, ketones or their derivatives from crude extracts of *Bupleurum scorzonerifolium*.

A majority of antineoplastic components isolated from *Bupleurum scorzonerifolium* contain a Y-butyrolactone centred heterocyclic compound forming Z or E configuration at carbon 2(5) as shown in Formula (I) or pharmacologically compatible salts, esters, ketones and their derivatives.

Formula (I)

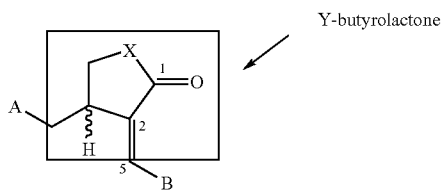

where the heterocyclic compound may have a 3R or 3S configuration, X can be N, O, S, or Se, and A and B can be selected from the following substituents:

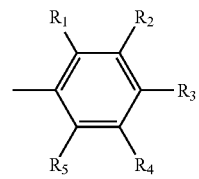

where R1, R2, R3, R4, R5 can be selected from a hydrogen atom, a halogen atom, a hydroxyl group, a sulfoxyl group, an amino group, a methoxyl group, and/or a nitro group In addition, Formula (I) further comprises novel heterocyclic compounds named chaihulactone, isochaihulactone and their derivatives as shown in Formula (II) and Formula (III). Chaihulactone, isochaihulactone and related analogues or derivatives of chaihulactone belong to a lignan skeleton. By comparing the formulae (I) (II) and (III), it is known that both chaihulactone and isochaihulactone are Y-butyrolactone centred heterocyclic compounds forming Z or E configuration at carbon 2(5).

Formulae (II)

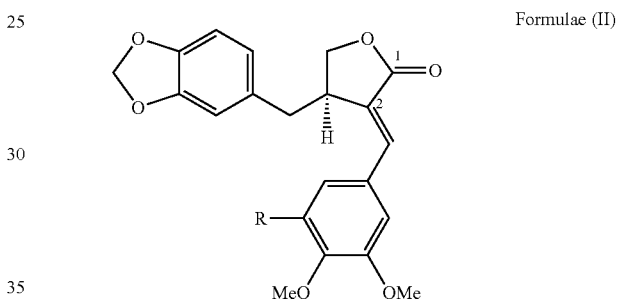

where R represents a methoxyl group.

Formulae (III)

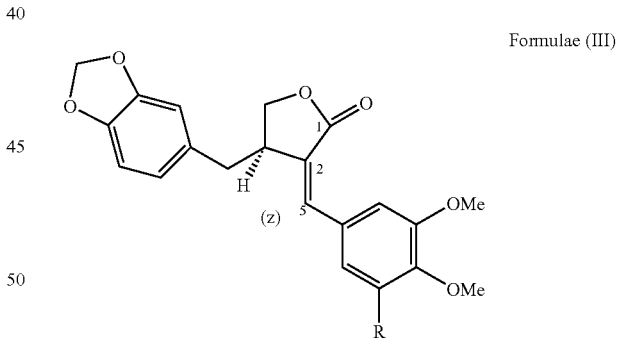

where R represents a hydrogen atom, a methoxyl group, or an aromatic group.

From the experimental results of the preferred embodiment invention it is found that different extracts containing the Y-butyrolactone centred heterocyclic compounds isolated from *Bupleurum scorzonerifolium* using different solvents (such as acetone or methanol) can all inhibit proliferation of tumor cells to some extent. And among different extracts isolated, the acetone crude extract provides the most effective antineoplastic effects among them. A partition and chromatographic method is further employed to isolate and purify antineoplastic components present in the *Bupleurum scorzonerifolium* acetone crude extract and analyse the molecular structure of those antineoplastic components, so as to identify novel heterocyclic compounds such as "chaihulactone, isochaihulactone and chaihulactone related analogues or derivatives".

From the experimental results of the preferred embodiments of the invention, it is found that as the antineoplastic components including chaihulactone, isochaihulactone and chaihulactone related analogues or derivatives are added to cell lines of human lung cancer, hepatoma, malignant gioblastoma, and colorectal carcinoma, the telomerase activity of the tumor cells treated with the antineoplastic components is significantly reduced when compared to that of the untreated group. A prominent cytotoxic effect was shown when the antineoplastic components are added to the Taxol-resistant tumor cell lines. These antineoplastic components contain Y-butyrolactone centred heterocyclic compounds forming Z or E configuration at carbon 2(5) or other pharmacologically compatible salts, esters, ketones and their derivatives. Moreover, it is found that chaihulactone and isochaihulactone and their derivatives are the most prominent antineoplastic components to tumor cells and thus serve as the main active antineoplstic agents in this invention.

The extracting method for isolating from *Bupleurum scorzonerifolium* Y-butyrolactone centred heterocyclic compounds and their derivatives that have inhibitory effects on tumor cells is provided as follow. The extracting method comprises two stages. At the first stage, several extracting layers are isolated from *Bupleurum scorzonerifolium* using solvents with opposite polarity. Then, a chromatographic method is used at the second stage to isolate a pure extract from a particular crude extract of *Buplerum scorzonerifolium* (from the first stage). The method for isolating the antineoplastic components from *Bupleurum scorzonerifolium* Wild is described below.

The *Bupleurum scorzonerifolium* powders are submerged in acetone. By repetitive extraction and concentration, *Bupleurum scorzonerifolium* acetone crude extract (known briefly hereinafter as BS-AE) is obtained, while the residues are extracted using methanol to obtain *Bupleurum scorzonerifolium* methanol crude extract (known briefly as BS-ME hereinafter). Lastly, the rest of the residues are further extracted using water to obtain *Bupleurum scorzonerifolium* water crude extract (known briefly as BS-WE hereinafter).

BS-AE is then dissolved in methanol solution. And after extraction using n-Hexane, *Bupleurum scorzonerifolium* n-Hexane extract (known briefly as BS-HE hereinafter) and *Bupleurum scorzonerifolium* methanol solution extract are isolated.

Methanol present in the methanol solution extract is removed and repeatedly extracted using chloroform ($CHCl_3$).

The chromatographic method is employed to isolate *Bupleurum scorzonerifolium* chloroform extract into elution fractions of methanol/dichloromethane with different concentrations and the elution fractions are concentrated.

The eluted fractions of methanol/dichloromethane are further isolated and purified by the chromatographic method to obtain pure compounds.

During the processes of extracting and fractionating the BS-AE, BS-ME, bioscreens for anticancer activity in each extracts or eluates from *Bupleurum scorzonerifolium* are applied. In addition, the molecular weights and structures of the antineoplastic components isolated from active elutes of *Bupleurum scorzonerifolium* are studied and identified using mass spectrometry and nuclear magnetic resonance spectrometry. And the antineoplastic components are found to contain Y-butyrolactone centred heterocyclic structures, which further suggesting the extraction method provided by the invention is capable of isolating the antineoplastic components present in Chinese herbs.

Furthermore, the inhibition of telomerase activity is observed in TRAP assay after the addition *Bupleurum scorzonerifolium* extracts. It is found that BS-AE is capable of providing effective inhibition to the telomerase activity and hTERT expression on human lung cancer cell lines, suggesting the potential of BS-AE to produce effective cytotoxicity to cancer cells with high specificity.

In particular, after adding the BS-AE, chaihulactone analogues or derivatives to Taxol-resistant tumor cells such as A549-T12 cells (A549 cells resistant to Taxol), it is found that the Y-butyrolactone centred heterocyclic compounds and their derivatives present in *Bupleurum scorzonerifolium* is capable of eliciting apoptosis of Taxol-resistant tumor cells. From the results of flow cytometric analysis and Western blotting analysis to study the mechanism of *Bupleurum scorzonerifolium* extracts, it is found that BS-AE can elicit high expression of tumor suppressors p21 and p53. As a result, the tumor cells are arrested at the spindle polymerisation stage (G2/M stage) of the cell cycle. Thus, in view of cell cycle regulation, the Y-butyrolactone centred heterocyclic compounds present in BS-AE can serve as a microtubule stabilizing agent, having a mechanism similar to that of paxlitaxel, since both enhance microtubule polymerization. As a result, the tumor cells are arrested at G2/M stage and subsequently become junk cells leading to apoptosis.

BRIEF DESCRIPTION OF THE DRAWINGS

The present invention can be more fully understood by reading the following detailed description of the preferred embodiments, with reference made to the accompanying drawings, wherein:

FIGS. 2A through to FIG. 2D illustrate the cell cycle peak change detected using flow cytometry for A549 cells treated with *Bupleurum scorzonerifolium* extracts: acetone extract (BS-A), methanol extract (BS-M) and water extract (BS-W) isolated according to the extracting method of the invention;

FIG. 20 is a blotting result of RT-PCR for mRNA expression of hTERT in the A549 cells treated with acetone extract (AE), methanol extract (ME), and water extract (WE) from selected Chinese herbs H1, H2, H3, and H4 (wherein H3 represents *Bupleurum scorzonerifolium*), and in the cells which are either untreated (B), or treated with DMSO at low (D1) and high (D2) concentrations (where FL represents hTERT in full length and β as a spliced variant form of hTERT subunit).

DETAILED DESCRIPTION OF THE PREFERRED EMBODIMENTS

Figure 1:
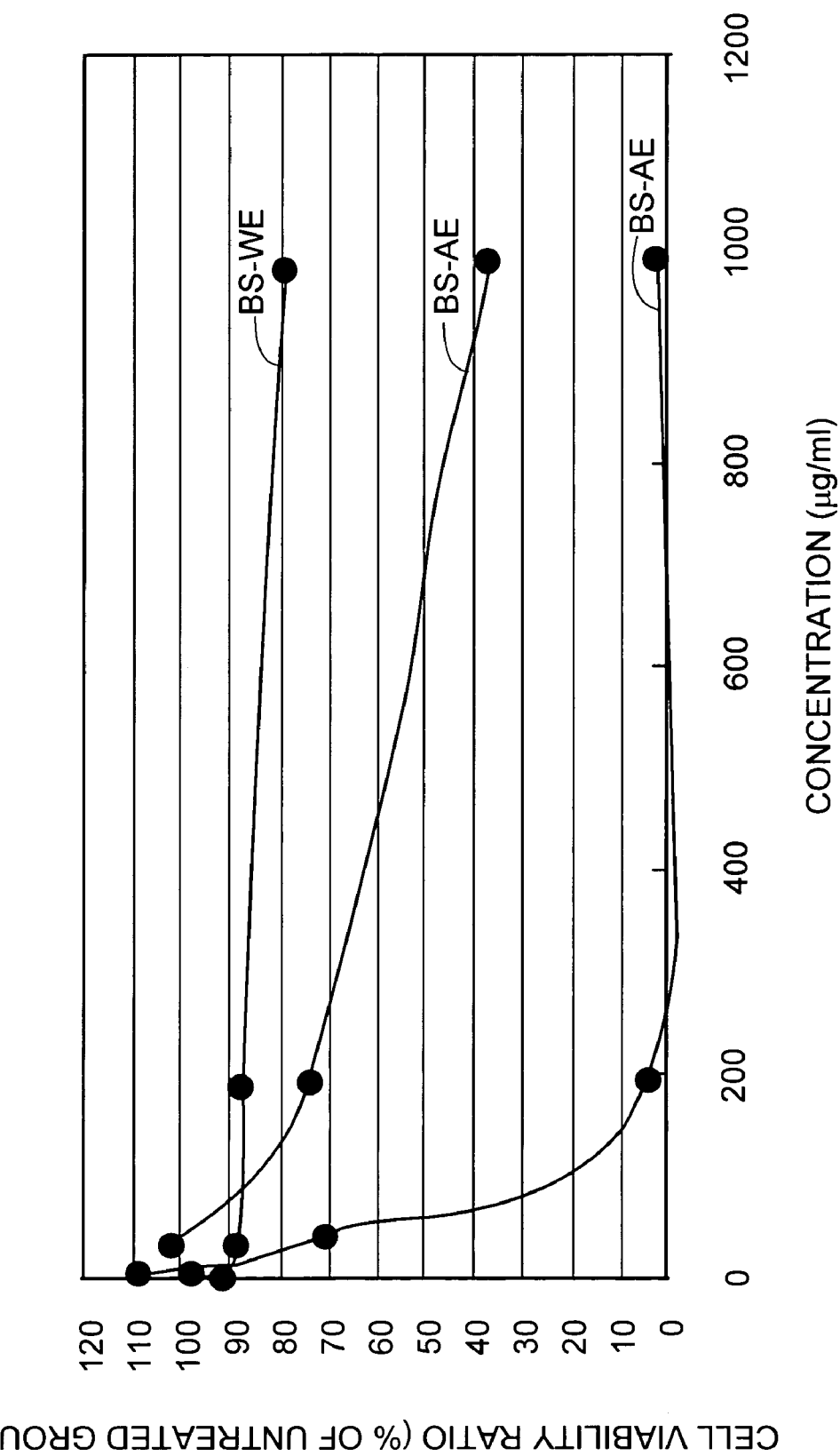
FIG. 1 is a schematic diagram showing change in cell viability ratio (in percentage of untreated group) for human lung cancer cell lines (A549 cells) subjected to a Methyl Thiazole Tetrazolium (MTT) assay with respect to the dosage (μg/ml) of *Bupleurum scorzonerifolium* extracts, such as Acetone Extract (BS-AE), Methanol Extract (BS-ME) and Water Extract (BS-WE) isolated according to the extracting method of the invention.

The present invention is described in detail in the following embodiments provided herein. It is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

This invention comprises at least 3 sections:

First of all, a method is described for extracting antineoplastic components from *Bupleurum scorzonerifolium* that have inhibitory effects to human hepatoma cell line J5, ovarian cancer cell line OVCAR-3, human malignant glioblastoma cell line DBTRG-05MD, lung cancer cell line A549, colorectal cancer cell line HT29, and A549 taxol-resistant subclone cells (A549-T12).

Secondly, after the extraction method, y-butyrolactone centred heterocyclic compounds with Z-configuration or E-configuration at carbon 2(5) are isolated from the *Bupleurum scorzonerifolium* extracts. Besides, pharmacologically compatible salts, esters, ketones and their analogical derivatives can be attached to those heterocyclic compounds. In addition, those heterocyclic compounds further comprise novel compounds, such as chaihulactone, isochaihulactone, as well as chaihulactone-related analogues and their derivatives.

Third, those with γ-butyrolactone-centred heterocyclic compounds, such as *Bupleurum scorzonerifolium* acetone crude extracts, chaihulactone, isochaihulactone, chaihulactone analogues and its derivatives, or pharmaceutical acceptable salts, esters, and ketones are tested on tumor cell lines both in vivo and in vitro to examine the inhibitory effects on tumor cells.

In accordance with the *Bupleurum scorzonerifolium* extraction method in the preferred embodiments of the invention, *Bupleurum scorzonerifolium* are grinded and submerged in acetone. After repetitively stirring, extracting and concentrating for four times, *Bupleurum scorzonerifolium* acetone crude extract (BS-AE) is obtained. The residues are extracted again in methanol, and the extract is called *Bupleurum scorzonerifolium* methanol crude extract (BS-ME). The residues are then extracted in water to obtain *Bupleurum scorzonerifolium* water extract (BS-WE). Subsequently, BS-AE is dissolved in methanol aqueous solution and extracted using n-Hexane solution to obtain *Bupleurum scorzonerifolium* n-hexane extract (BS-HE) and *Bupleurum scorzoneri-*

*folium* methanol water extract. The methanol in *Bupleurum scorzonerifolium* methanol water extract is then partitioned in chloroform and *Bupleurum scorzonerifolium* chloroform extract (BS-CE) is obtained by repetitive extraction and concentration in chloroform. Chromatography based method is then utilised to isolate the BS-CE and collect individual fractions after each methanol/dichloromethane elution. Lastly, chromatography (such as silica gel chromatography), preparative HPLC is used to isolate and purify active methanol/dichloromethane elution fraction, in order to obtain active pure compounds.

The molecular mass and structure of each pure compound isolated from chromatography are identified using mass spectrometry and nuclear magnetic resource spectrometry. The resultant heterocyclic compounds are tabulated as follows:

| Isolated Component | Structure Formulae | Molecular weight and structure |
|---|---|---|
| Component 1 | | 368.39<br>Kaerophyllin |
| Component 2 | | 398.41<br>Yatein |
| Component 3 | | 398.41<br>Chaihulactone |
| Component 4 | | 284.27<br>Oroxylin A |
| Component 5 | | 284.27<br>Wogonin |

-continued
| Isolated Component | Structure Formulae | Molecular weight and structure |
|---|---|---|
| Component 6 | 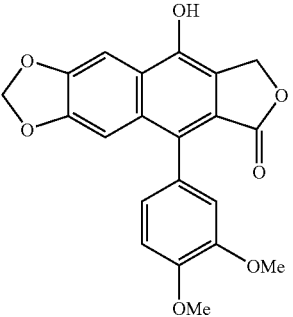 | 380.35<br>Chinensinaphthone |
| Component 7 | 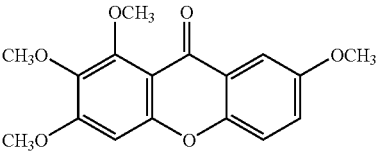 | 316.31<br>1,2,3,7-tetramethoxanthone |
| Component 8 | 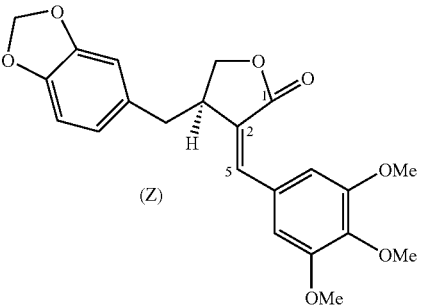 | 398.41<br>Isochaihulactone |
| Component 9 | 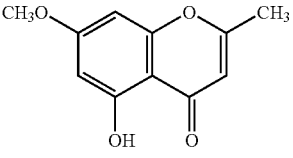 | 206.20<br>Eugenin |
| Component 10 | 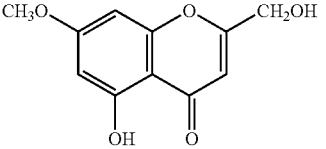 | 222.20<br>Saikochromone A |
| Component 12 | 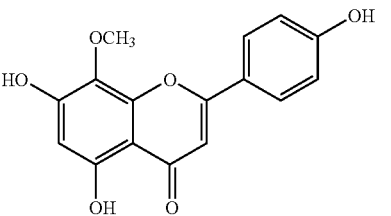 | 300.27<br>Isoscutellarein-8-methyl ether |

-continued

| Isolated Component | Structure Formulae | Molecular weight and structure |
|---|---|---|
| Component 14 | | 394.38<br>Chaihunaphthone |
| Component 15 | | 368.39<br>Isokaerophyllin |

Each of the aforementioned heterocyclic compounds from each extract as well as the acetone crude extracts of *Bupleurum scorzonerifolium* are assayed to measure the antineoplastic activity. It was shown that majority of antineoplastic components of *Bupleurum scorzonerifolium* are retained in the BS-AE and BS-ME. The BS-HE and BS-CE hardly have any tumor-suppressing effects. Besides, the extracts can be further purified using chromatography method (e.g. low pressure liquid chromatography or high performance liquid chromatography (HPLC)), such that fractions are collected separately after each elution to obtain the pure compounds mentioned above.

From the results obtained from drug screening of the preferred embodiment of the invention, among those components isolated using chromatographic method, the eighth component is found to have the most prominent anti-tumor effects to human hepatoma, lung cancer, ovarian cancer, malignant glioblastoma and colorectal cancer. Moreover, from chemical analysis of the main representative molecular structure of the eighth component, it was observed that the compound shares a common feature shown in formula (I) as having a γ-butyrolactone-centred heterocyclic compound with Z configuration or E configuration at carbon 2(5), or pharmacologically compatible salts, esters, ketones or their derivatives.

Formula (I)

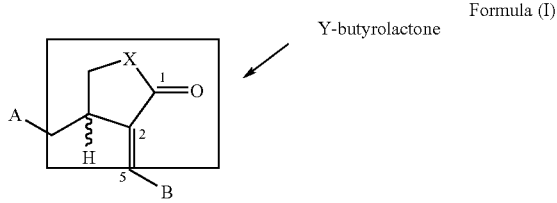

where the heterocyclic compound may have a 3R or 3S configuration, X can be N, O, S, or Se, andA, B can be selected from the following substituents:

where R1, R2, R3, R4, R5 can be selected from hydrogen atom, a halogen atom, a hydroxyl group, a sulfoxyl group, an amino group, a methoxyl group, and a nitro group.

When the third, eighth, fourteenth and fifteenth components are further analysed, it is found a novel group of heterocyclic compounds present in *Bupleurum scorzonerifolium* extracts. These novel heterocyclic compounds are published for the first time and are named as Chaihulactone, Isochaihulactone and Chaihulactone-related analogues or derivatives, such as Chaihunaphthone. And among these compounds, the chaihulactone and isochaihulactone are both γ-butyrolactone centred heterocyclic compounds and have Z-configuration or E-configuration at carbon 2(5). The formulae of chaihulactone analogues and isochaihulactone analogues are shown by Formula II and Formula III, respectively:

Formulae (II)

Where R represents a methoxyl group.

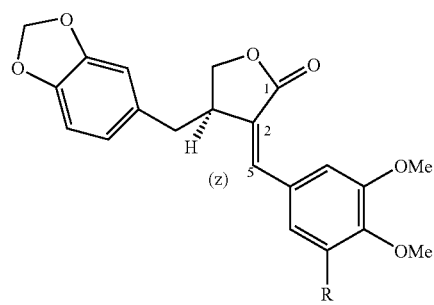

Formulae (III)

where R represents hydrogen atom, a methoxyl group, or an aromatic group.

These novel heterocyclic compounds, i.e. Chaihulactone, Isochaihulactone and Chaihulactone analogues or derivatives, belong to a kind of lignan, which is present in *Bupleurum scorzonerifolium* dried mixture. It was found that BS-AE and isochaihulactone have the most significant tumor-suppressing effects among all those types of *Bupleurum scorzonerifolium* extracts described above. Therefore, the BS-AE and isochaihulactone are used as standard anti-tumor components for *Bupleurum scorzonerifolium* contained γ-butyrolactone and *Bupleurum scorzonerifolium* novel compounds to demonstrate the function of tumor suppression effect on human hepatoma, ovarian cancer, lung cancer, malignant glioblastoma and colorectal carcinoma.

The γ-butyrolactone-centred heterocyclic compounds, such as chaihulactone analogues are also used as indicators to examine the efficacy of *Bupleurum scorzonerifolium* extracts to inhibit tumor growth on cultured cell lines and animal models.

From the results of in vitro and in vivo study according to the preferred embodiments of the invention, it clearly indicated that BS-AE could effectively reduce tumor volume, induce nuclear fragmentation for tumor cell and lymphocyte infiltration, and result in a large area of necrosis of tumor tissue. Moreover, from the results of toxicity test on animals, the mammalian models do not show significance differences in terms of internal organ functionality indicators, such as lipase, amylase, cretonne kinase, lactate dehydrogenase, GOT, BUN before or after BS-AE is applied to mammalian models. However, the telomerase activity of the tumor cell was decreased significantly after application of BS-AE. Thus, it is demonstrated that administration of the BS-AE and the compounds, such as "chaihulactone, isochaihulactone and chaihulactone analogues or derivatives," on mammals could exert highly specific cytotoxicity to human hepatoma, ovarian cancer, lung cancer, malignant glioblastoma and colorectal cancer without damaging normal liver and kidney functions.

On the other hand, when the BS-AE containing γ-butyrolactone heterocyclic compounds, such as isochaihulactone and BS-AE are applied on Taxol-resistant tumor cell line, for example, human lung cancer cell line A549-T12, they also show anti-tumor effects on the resistant tumor cells. The results demonstrate the concentration of isochaihulactone that causes 50% growth inhibition ($IC_{50}$) is 2-4 μg/mL. This indicates that the most dominant tumor-suppressing active components in *Bupleurum scorzonerifolium* are chaihulactone, isochaihulactone and chaihulactone-related analogues and their derivatives. Furthermore, the tumor-suppressing effects of those *Bupleurum scorzonerifolium* extracts after isolated by the extraction method of this invention are more prominent.

Therefore, in view of the mechanism of *Bupleurum scorzonerifolium* extracts (especially BS-AE, chaihulactone, isochaihulactone and chaihulactone analogues or derivatives), BS-AE and isochaihulactone act as a microtubule stabilizing agent to repress mitosis in a similar manner as paclitaxel. However, these two drugs may act on different targets of β-tubulin.

In summary, in the search of new drug, the novel compounds, such as "chaihulactone, isochaihulactone, chaihulactone analogues or derivatives," isolated from *Bupleurum scorzonerifolium* could potentially become the new anti-cancer agents.

PREFERRED EMBODIMENTS

The present invention will be explained in detail with all the tables and figures on the following subjects: (1) the antineoplastic effects of *Bupleurum scorzonerifolium* extracts, (2) bioscreen-guided fractionation of *Bupleurum scorzonerifolium*, (3) the preferred embodiments of methods for extracting the active extracts or components from *Bupleurum scorzonerifolium* in treating human hepatoma, ovarian cancer, lung cancer, malignant glioblastoma and colorectal carcinoma. The following embodiments are meant to provide the best modes for carrying out the present invention, rather than to limit the scope of the invention to the disclosed embodiments. And when *Bupleurum scorzonerifolium* extracts and their active components are made into pharmacologically compatible salts, esters, ketones or analogues, the composition, formulation, and synthesizing method thereof can be adjusted according to the practical circumstances.

First Embodiment

Extraction Method of Antineoplastic Extracts and Compounds from *Bupleurum scorzonerifolium*

*Bupleurum scorzonerifolium* used in this invention is radix Bupleuri of Umbelliferae family. After drying and grinding of the *Buleurum scorzonerifolium* plant tissue, 6 kg of *Bupleurum scorzonerifolium* powder is submerged and stirred within 20 L acetone at room temperature for 4 hours and extracted 4 times repeatedly to obtain the *Bupleurum scorzonerifolium*-acetone crude extract (BS-AE). Methanol is added to the residues to obtain *Bupleurum scorzonerifolium*-methanol extract (BS-ME). Then water is added to the residue to obtain *Bupleurum scorzonerifolium*-water extract (BS-WE). Then 95% methanol solvent is used to dissolve BS-AE. After partition with n-hexane for 3 times, *Bupleurum scorzonerifolium*-hexane (BS-H) and *Bupleurum scorzonerifolium*-methanol (BS-M) are isolated. 500 ml of distilled water is then added to remove the methanol in BS-M layer. Next, chloroform is added to methanol-free BS-M to carry out further partition. After partition with chloroform for 3 times, chloroform was concentrated to produce *Bupleurum scorzonerifolium*-chloroform extract (BS-CE).

MTT assay is used to test the cytotoxic effect of BS-AE, BS-ME, BS-HE, BS-CE and BS-WE on human hepatoma cell line J5, ovarian cancer cell line OVCAR-3, human malignant glioblastoma cell line DBTRG-05MD, lung cancer cell line A549 and colorectal cancer cell line HT29. Table 1 shows that extracts from BS-AE and BS-CE have the best antineoplastic effect among all Bupleurum scorzonerifolium extracts. According to the extraction steps "BS-AE→BS-CE" all of the extracts contain the antineoplastic components. In order to further isolate the antineoplastic components a "Chromatography" step is further employed to isolate each antineoplastic component from BS-CE.

A Silica Gel Chromatography is employed to elute 100 g BS-CE with 5% methanol/dichloromethane, 10% methanol/dichloromethane, 20% methanol/dichloromethane and methanol to obtain 27.5 g 5% methanol/dichloromethane, 14.04 g 10% methanol/dichloromethane, 10.96 g 20% methanol/dichloromethane and 7.25 g extract respectively. The antineoplastic compounds are retained mainly in the 5% methanol/dichloromethane extract. Then, preparative High Performance Liquid Chromatography (HPLC), Medium Pressure Liquid Chromatography (MPLC), Lobar, and other chromatographic methods are employed to isolate the 5% methanol/dichloromethane extract, as well as to further concentrate the third, eighth, fourteenth and fifteenth fractions isolated from the antineoplastic compounds.

Second Embodiment

Structure of Antineoplastic Components from *Buplerum scorzonerifolium* Wild

Mass Spectrum and Nuclear Magnetic Resonance Spectrum (NMR) are employed to determine the molecular weight and the structure of the third, eighth, fourteenth and fifteenth fractions isolated from the BS-AE, the mass spectrum is shown in the table 2 below:

TABLE 2 the components isolated from the antineoplastic compounds in BS-AE

| Low pressure liquid chromatography | Structure formulae | Molecular weight and structure |
|---|---|---|
| Component 3 | 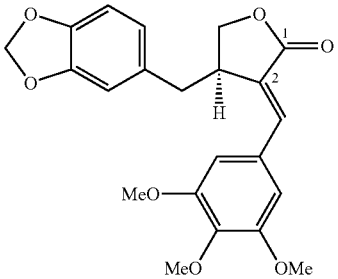 | 398.41<br>Chaihulactone |
| Component 8 | 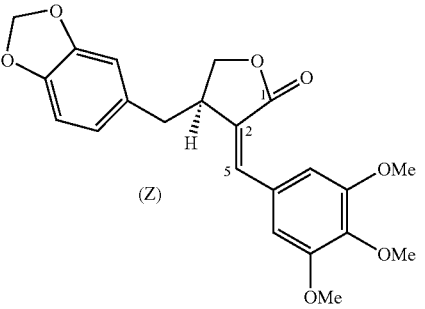 | 398.41<br>Isochaihulactone |
| Component 14 | 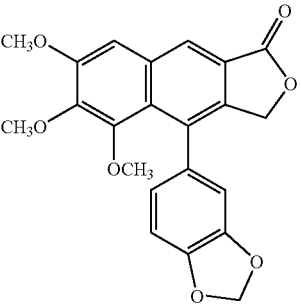 | Chaihunaphthone |

TABLE 2-continued the components isolated from the antineoplastic compounds in BS-AE

| Low pressure liquid chromatography | Structure formulae | Molecular weight and structure |
|---|---|---|
| Component 15 | 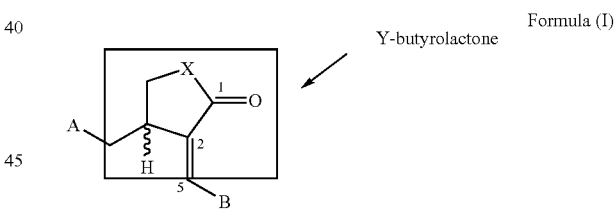 (Z) | Isokaeophyllin |

After analyzing the molecular structures, it is appreciated that the pure compound (isochaihulactone) isolated from *Bupleurum scorzonerifolium* shows inhibitory effect on tumor cells of human hepatoma, ovarian cancer, lung cancer, malignant glioblastoma and colorectal carcinoma. γ-butyrolactone is the central structure of the compound, and forms Z and E configurations of heterocyclic compounds at carbon 2(5). Therefore hydrogen-nuclear magnetic resonance ($^1$H-NMR) and carbon 13-nuclear magnetic resonance ($^{13}$C-NMR) are used to further analyze the molecular structures of the crystallized structure of the third and eighth components, to obtain two novel compounds "chaihulactone" and "isochaihulactone" which are shown as formulae I and II.

Formula (I)

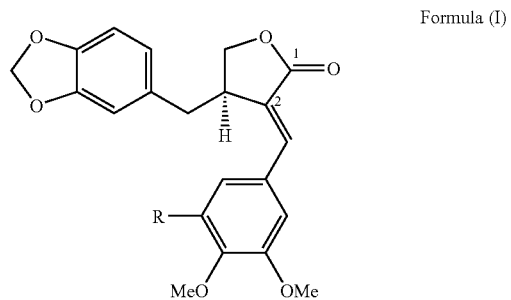

where R represents a methoxyl group.

Formula (II)

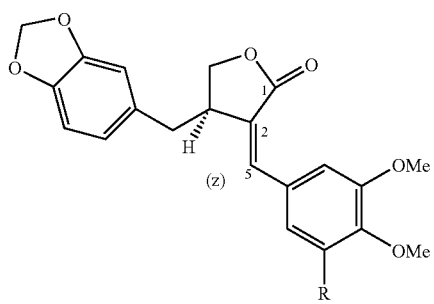

where R represents a hydrogen atom or a methoxyl group. (white needle crystal, melting point of 137-138° C., $[\alpha]_D^{25}$ −29.0° (c0.5,CHCl3); IR (KBr) $\nu_{max}$ cm$^{-1}$: 1745, 1635, 1581, 1335, 1153; UV (CHCl3) $\lambda_{max}$ nm (log ϵ): 247(4.08), 298(4.17), 327(4.08))

In addition, other compounds, which show antineoplstic effects, for example the representative components and their analogues and derivatives from the foregoing first, second, eleventh, and fifth components are analyzed and compared with current pharmaceutical database. The result of the comparison indicates that all of the antineoplastic components extracted from the *Bupleurum scorzonerifolium* contain γ-butyrolactone as a central structure, and all of them has a heterocyclic compounds at carbon position 2(5) that can be attached with salts, esters, ketones or their derivatives. The formula (I) of the heterocyclic compounds is listed as follows:

Formula (I)

γ-butyrolactone where the heterocyclic compounds may have a 3R-form or 3S-form, X can be N, O, S, or Se; and A, B can be selected from the following substituents:

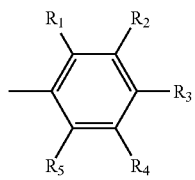

where R1, R2, R3, R4, R5 can be selected from a hydrogen atom, a halogen atom, a hydroxyl group, a sulfoxyl group, an amino group, a methoxyl group, and a nitro group and the substituents further comprise the following structures:

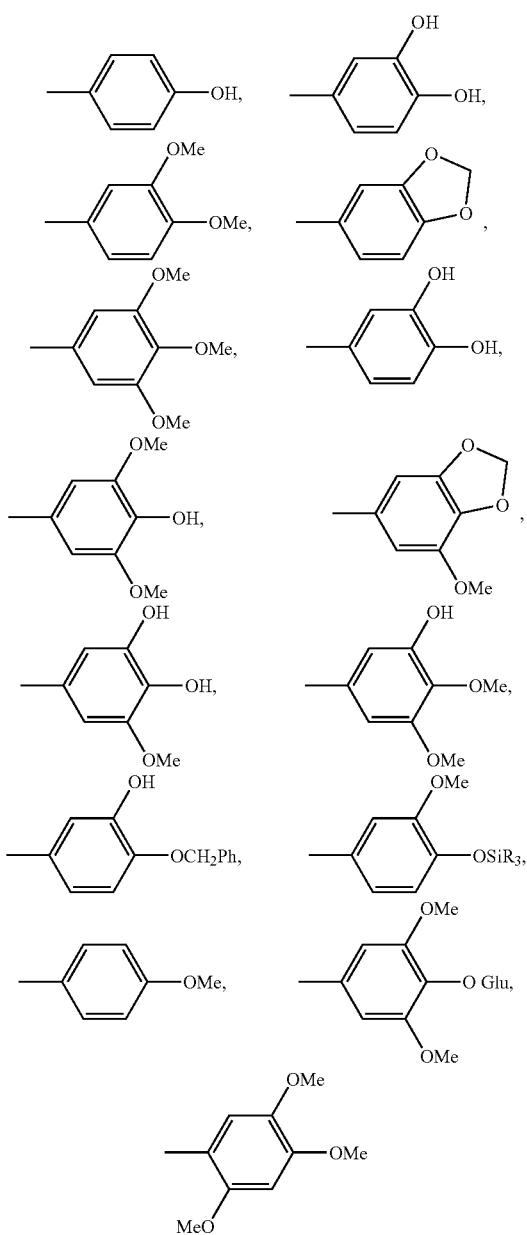

The evaluation of the cytotoxicity shows that the antineoplastic components of the eighth fraction extracted from Isochaihulactone elicits more prominent anti-tumor effect on tumors of lung cancer, human malignant glioblastoma and colorectal cancer, compared to the other Chaihulactone liked compounds. Therefore, the following embodiments of the invention all use the BS-A extract and the Isochaihulactone component (BS-(8)) in the eighth fraction to evaluate the efficacy of γ-butyrolactone and the heterocyclic compounds and the novel compounds comprising of Chaihulactone, Isochaihulactone, Chaihulactone and their derivatives.

Third Embodiment

The Effect of *Bupleurum scorzonerifolium* Extracts on Cell Proliferation

BS-AE, BS-ME, BS-WE are added to cell cultures of J5, Ovcar-3. A549, DBTRG-05, and HT-29, respectively, and the tumor cell growth inhibition effect from each tissue culture was observed during the 3 days treatment. The cytotoxicity was measured using MTT assay and $IC_{50}$ values of *Bupleurum scorzonerifolium* extracts for A549 cells were shown in FIG. 1. Therefore it is concluded that the most effective antineoplastic compounds from *Bupleurum scorzonerifolium* is mainly present in BS-AE.

Furthermore, flow cytometry is employed to observe the changes in cell cycle before and after the addition of different extracts from *Bupleurum scorzonerifolium* to A549 cells. In FIGS. 2A through to 2D, X-axis represents chromosome numbers (2N, 4N, etc.) of tumor cells in contact with the antibody, Y-axis represents the fluorescent brightness of Propidium Iodide (PI). It is clearly noted that before treatment lung cancer cell line A549 is mainly at stage of G0/G1, but when 60 μg/ml of BS-AE and 600 μg/ml of BS-ME are added to the tumor cells, the tumor cells are arrested at G2/M stage. This is particularly the case for BS-ME. So, it is suggesting that antineoplastic extracts from *Bupleurum scorzonerifolium* are likely to be associated with the mechanism underlying G2/M arrest.

Fourth Embodiment

*Bupleurum scorzonerifolium* Extracts and Apoptosis

In order to further prove the putative apoptosis effects of the *Bupleurum scorzonerifolium* extracts on the tumor cell line, the present embodiment of the invention uses flow cytometry, Reverse Transcription Polymerase Chain Reaction (RT-PCR), and Western Blotting analysis to monitor any change in tumor cell cycle and change in expression level of the regulation protein p21 and p53 after tumor cell lines are added with BS-AE and isochaihulcatone.

Figure 3A:
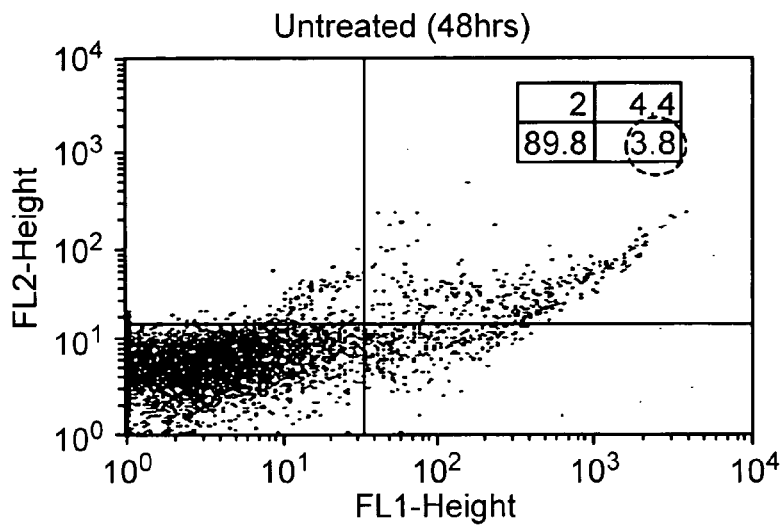
FIGS. 3A through to FIG. 3C are cytograms showing the extent of cell apoptosis detected using flow cytometry for A 549 cells either untreated, treated with 20 μM of isochaihulactone, or 60 μg/ml of BS-AE and cultured for 48 hrs (wherein X-axis indicates fluorescence intensity of tumor cells bound with Annexin V-FLOUS antibodies; and Y-axis indicates fluorescence intensity of tumor cells bound with PI antibodies)
Figure 3B:
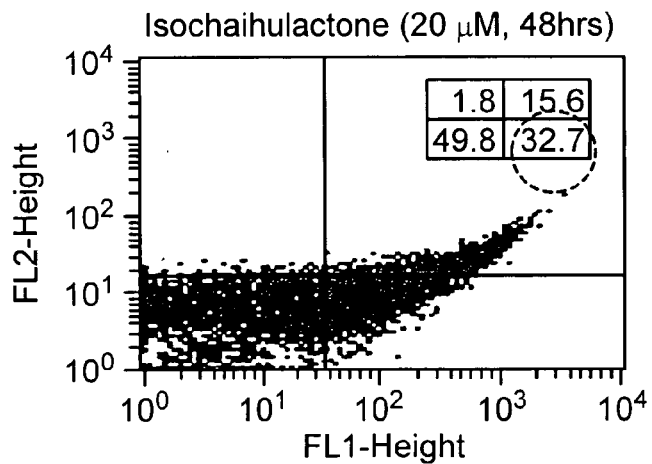
Figure 3C:
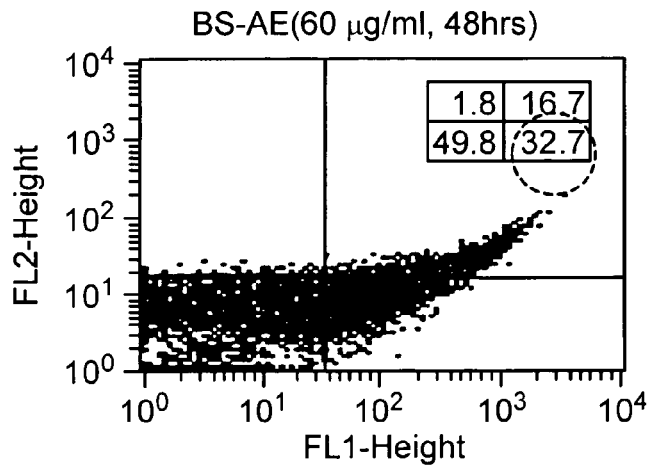

In A549 cells, 20 μM of Isochaihulactone and 60 μg/ml of BS-AE are added to A549 cell line. After 48 hours of treatment, flow cytometry is utilized to detect the staining results between Annexin V-FLOUS and PI. In FIGS. 3A through to 3C, X-axis represents the fluorescent brightness of tumor cells with antibody Annexin V-FLOUS, and Y-axis represents the fluorescent brightness of tumor cells with antibody PI. From the diagrams, it was shown that the untreated group has only 3.8% of apoptosis, whereas A549 cells treated with Isochaihulactone and BS-AE has much higher proportion of cell death (about 30-40%). These results strongly suggest that BS-AE and isochaihulactone may play a role in inducing apoptosis of the tumor cells.

Figure 4:
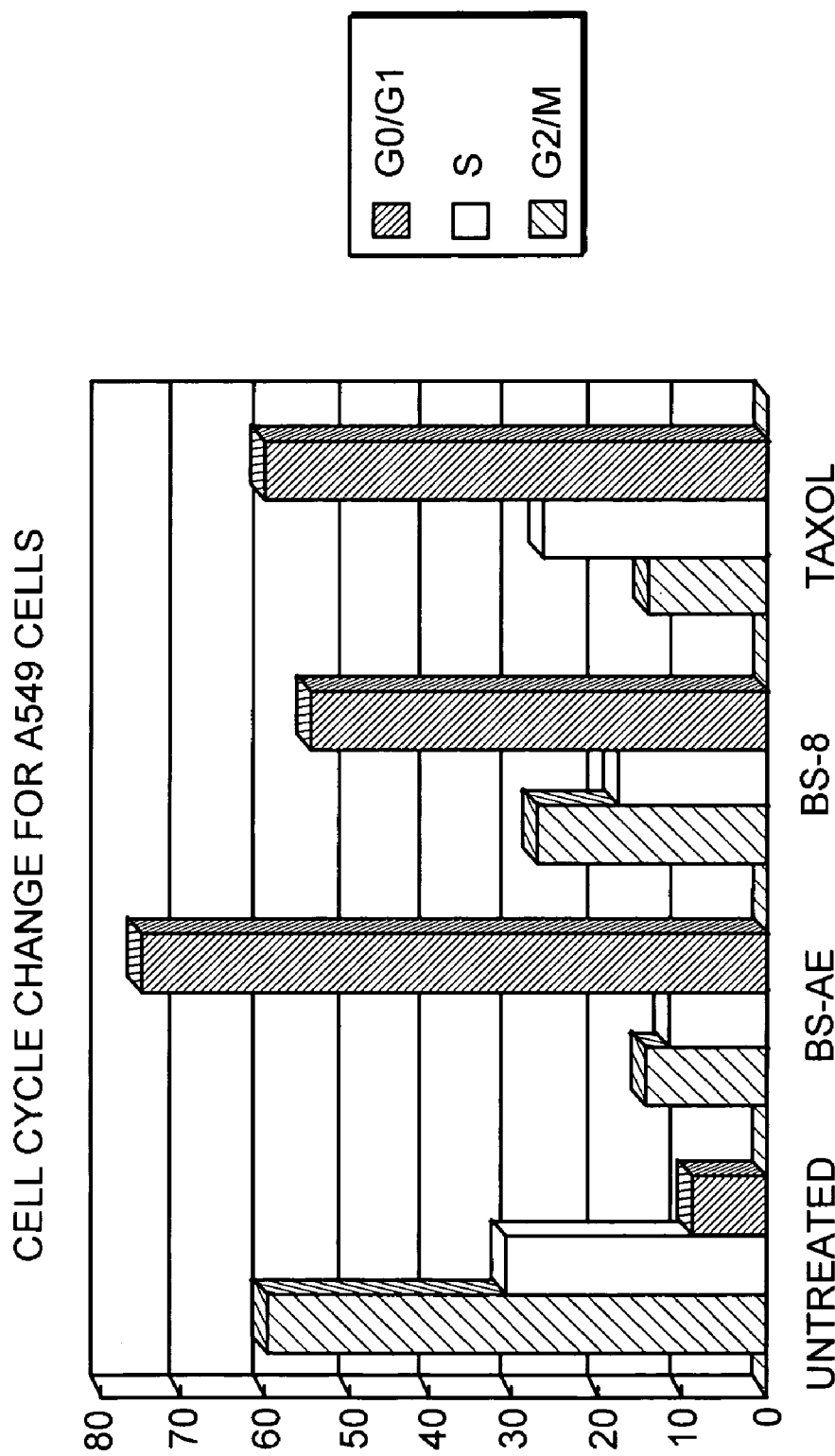
FIG. 4 is a bar chart showing cell cycle changes detected using flow cytometry for A549 cells untreated, treated with BS-AE, isochaihulactone (BS-8), and Taxol.
Figure 5:
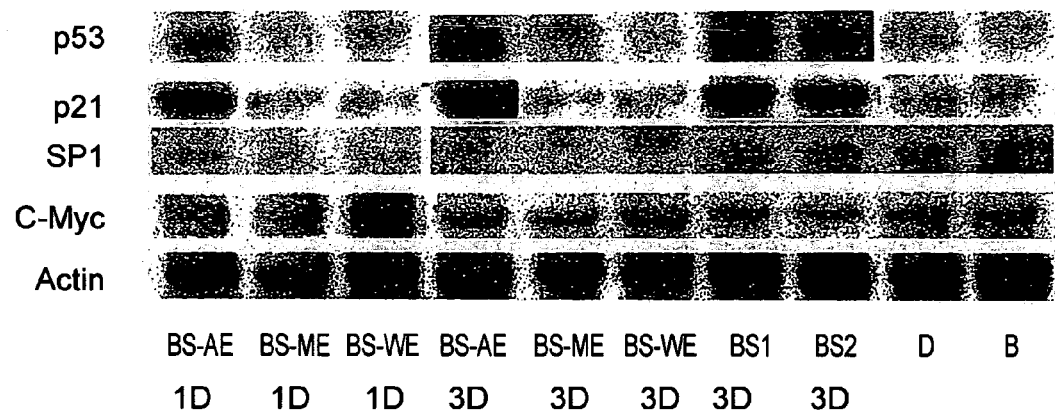
FIG. 5 is an immunoblot analysis diagram showing the amount of tumor suppressors: p21 and p53 expressed in A 549 cells either untreated (B), treated with DMSO (D) or BS-AE, BS-ME, BS-WE, isochaihulactone (BS-1), or chaihulactone (BS-2) for 1 day (1 D) or 3 days (3 D)

Therefore, from the Cell Cycle in FIG. 4 and the result of Western Blotting analysis in FIG. 5, it was apparent that BS-AE and isochaihulactone could induce the tumor cells to arrest at the stage G2/M. Moreover, both BS-AE and isochaihulactone result in a increase in expression level for tumor suppressor p21 and p53.

Therefore, from the results shown above, it should be apparent that BS-AE containing chaihulactone analogous or derivatives play a role in G2/M arrest resulting apoptosis on tumor cells. This apoptosis is also observed in human hepatoma, lung cancer, ovarian cancer, malignant glioblastoma and colorectal carcinoma, suggesting the BS-AE should have an inhibitory effect on the cell proliferation of cancer cells.

Figure 6:
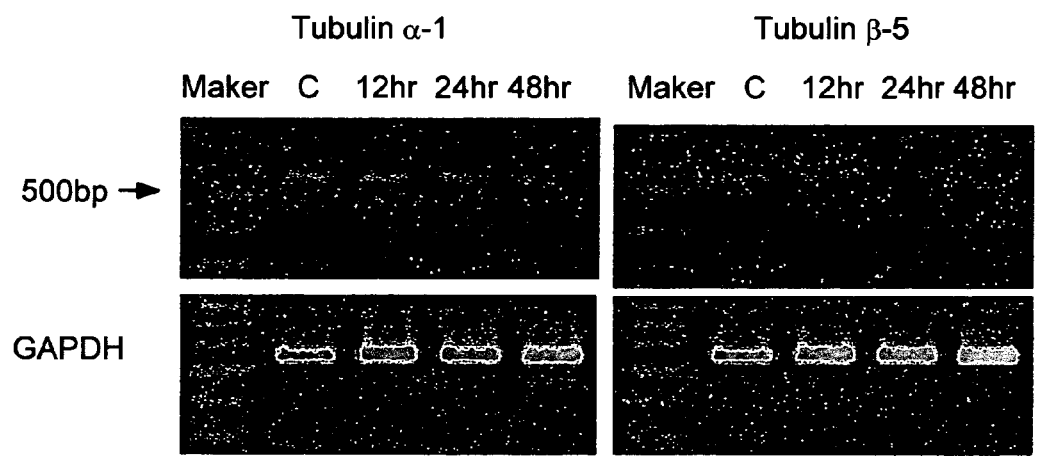
FIG. 6 is a blotting result of reverse transcriptase polymerase chain reaction (RT-PCR) showing messenger ribonucleic acid (mRNA) expression of type-1 α tubulin and type-5 β-tubulin in A549 cells either untreated (C), treated with BS-AE for 12 hrs, 24 hrs, and 48 hrs.
Figure 7:
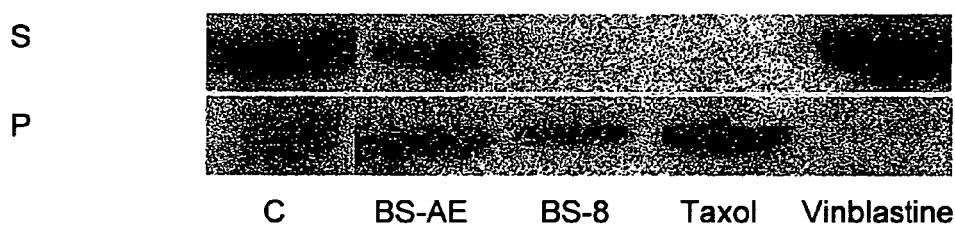
FIG. 7 is one further immunoblot analysis diagram showing expression of soluble (S) and particular (P) form of β-tubulin in A549 cells either untreated (C), treated with BS-AE, isochaihulactone (BS-8), Taxol, or Vinblastine.

Reverse transcriptase polymerase chain reaction (RT-PCR) is then used to analyze the change of cytoskeleton of tumor cell lines treated with *Bupleurum scorzonerifolium* extract. As shown in FIG. 6, the cytoskeleton of type-1 α-microtubule has no significant change after treating A549 cells with BS-AE for 12, 24 and 48 hrs. Instead, a gradual decrease in the number of type-V β-microtubule is detected. Then, a polymerization event is observed before and after the treatment of BS-AE. As shown in FIG. 7, after adding BS-AE and isochaihulactone, the soluble form (non-polymerized β-microtubule illustrated as S in the diagram) significantly diminishes, whereas the particular form (polymerized β-microtubule illustrated as P in the diagram) increases. This indicates that BS-AE and isochaihulactone have similar effect on the polymerization of tubulin as Taxol.

Figure 8:
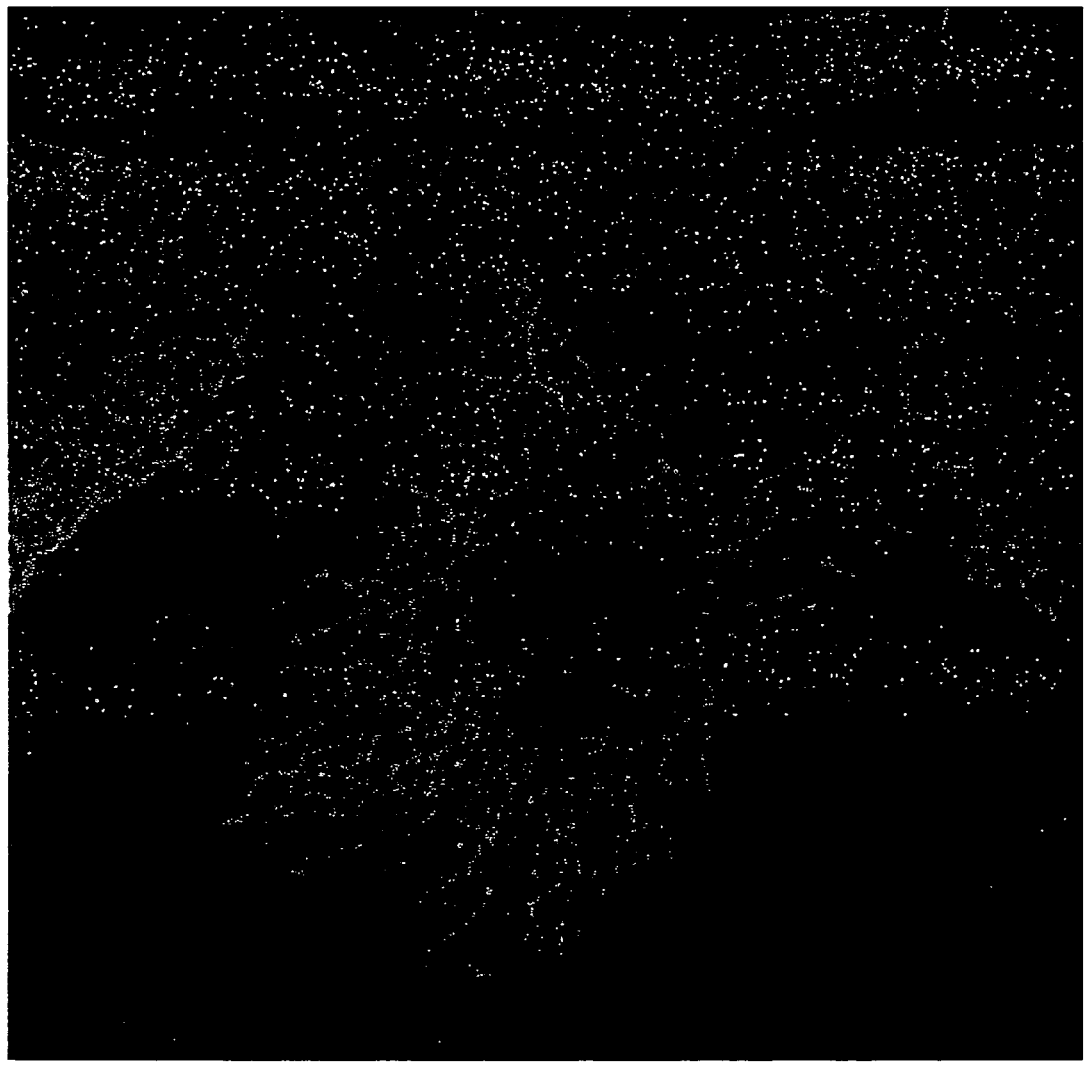
FIG. 8 is a confocal microscopic section showing elongation of spindles in the fluorescent labeled A549 cells treated with BS-AE.

Moreover, confocal microscopy is utilized to further analyze the arrangement of the spindle inside the cytoskeleton of the fluorescent-labeled microtubule. As shown in FIG. 8, after treatment of BS-AE to the tumor cells, the polymerization of β-tubulin results in the progressive elongation of spindle. Therefore, 2N or nN chromosomes are stopped from migrating towards the spindle poles and divisions of tumor cells are inhibited. In this way, tumor cells cannot progress through mitosis successfully with accumulation of 2N and 4N chromosomes, resulting in apoptosis of junk cells.

Fifth Embodiment

The effect of *Bupleurum scorzonerifolium* Extracts on Taxol-Resistant Tumor Cell Line Recent cell culture study shows no satisfactory toxicity effect on Taxol-resistant tumor cell at late stage of chemotherapy in vitro. The previous results from flow cytometry show that BS-AE, isochaihulactone and Taxol have similar inhibitory effect on cell growth of A549 cells. Therefore, the present invention is based on *Bupleurum scorzonerifolium* extracts as a new drug option to examine the cytotoxic effect of *Bupleurum scorzonerifolium* extracts on Taxol-resistant tumor cell line.

The following embodiments are described with Taxol-resistant tumor cell A549-T12 (passage cultured from lung cancer cell line A549 cells with low concentration of taxol) as an example to test the effect of BS-A and its pure compounds (these represent chaihulactone and chaihulactone analogues). Flow cytometry, cytotoxicity, and biomolecular examinations are adopted to estimate the mechanism of *Bupleurum scorzonerifolium* extracts on Taxol-resistant tumor cells.

Figure 9B:
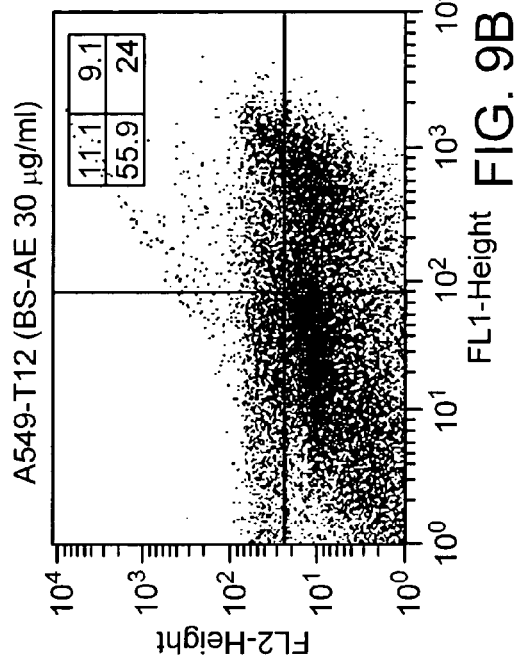
FIGS. 9A through to 9D are cytograms showing the extent of cell apoptosis detected using flow cytometry for Taxol-resistant human lung cancer cell lines (A549-T12 cells) either untreated, treated with BS-AE, isochalihulactone (BS-8), or isokaerophyllin (BS-15) for 24 hrs (wherein X-axis indicates fluorescence intensity of tumor cells bound with Annexin V-FLOUS antibodies; and Y-axis indicates fluorescence intensity of tumor cells bound with PI antibodies)
Figure 9D:
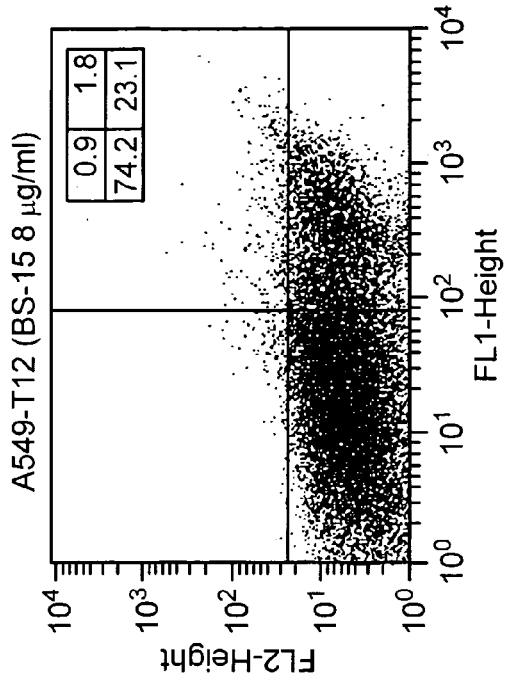
Figure 9A:
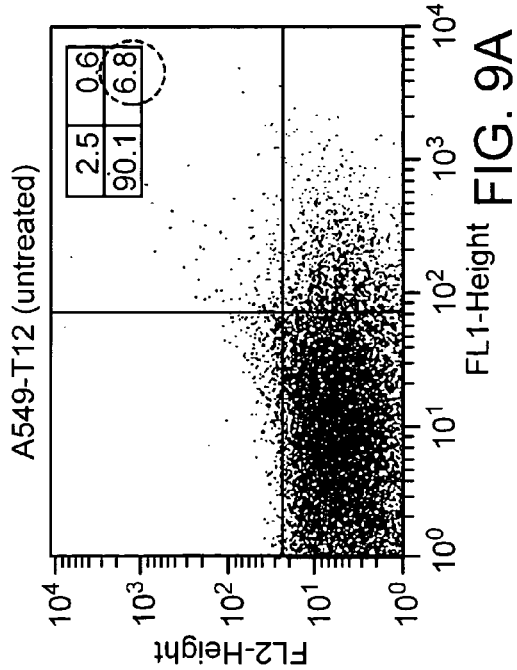
Figure 9C:
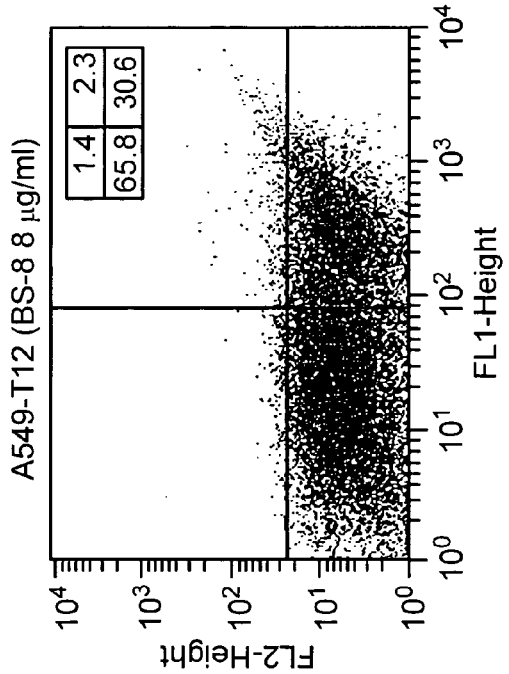

FIGS. 9A through to 9D show that flow cytometry is used to compare the change of Annexin V-FLOUS and PI for untreated group with that of the group treated with 100 nM of Taxol, 30 μg/ml BS-AE, 8 μg/ml BS-8 and 8 μg/ml BS-15 to A549-T12. Among these figures, X-axis represents the fluorescent brightness of tumor cells with antibody Annexin V-FLOUS whereas Y-axis represents the fluorescent brightness of tumor cell with antibody PI. The result shows that after 48 hours of treatment, there is 6.8% of apoptotic cells in the untreated group. However, after 48 hours of treatment, the A549-T12 cell line treated with isochaihulactone, chaihulactone analogues or BS-AE show that the ratio of apoptotic tumor cell significantly increase to 30.6%, 23.1% and 24% respectively. This indicates isochaihulactone has better induction for apoptosis of Taxol-resistant tumor cell line than other chaihulactone analogues. Furthermore, BS-AE is more effective for tumor cell apoptosis than crude extracts after purification.

Figure 10A:
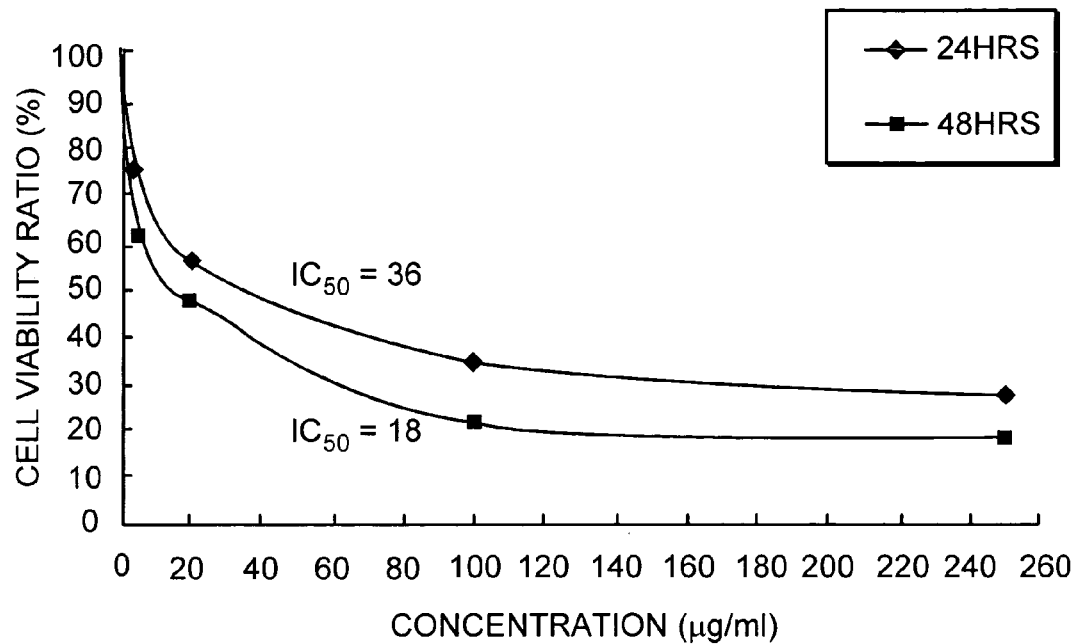
FIGS. 10A through to 10C illustrate results of MTT assays for A549-T12 cells treated with BS-AE, isochaihulactone (BS-8), and isokaerophyllin (BS-15) respectively for 24 hrs and 48 hrs.
Figure 10B:
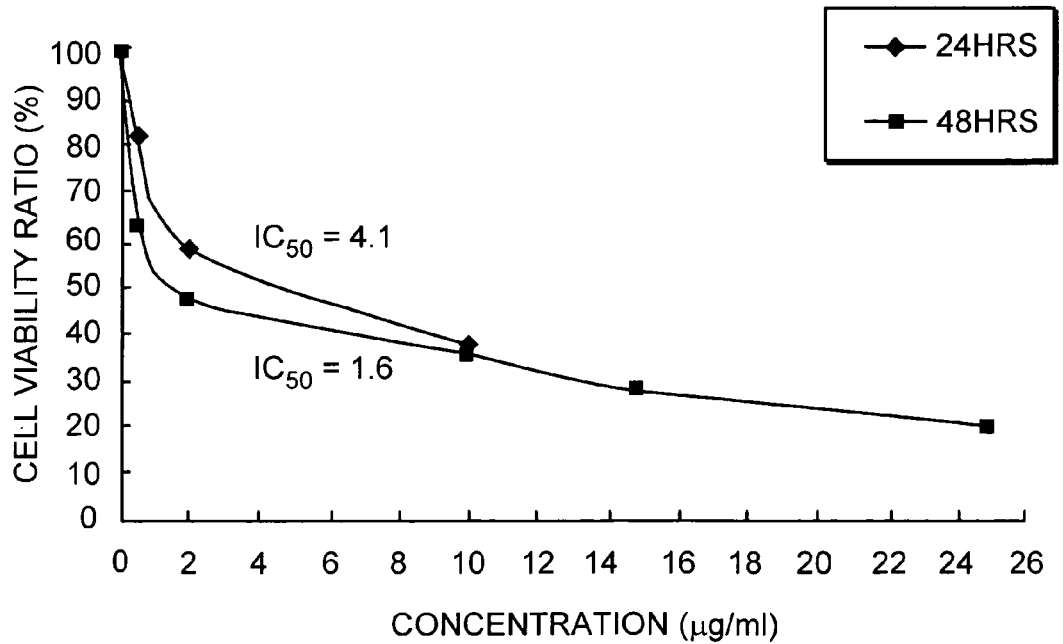
Figure 10C:
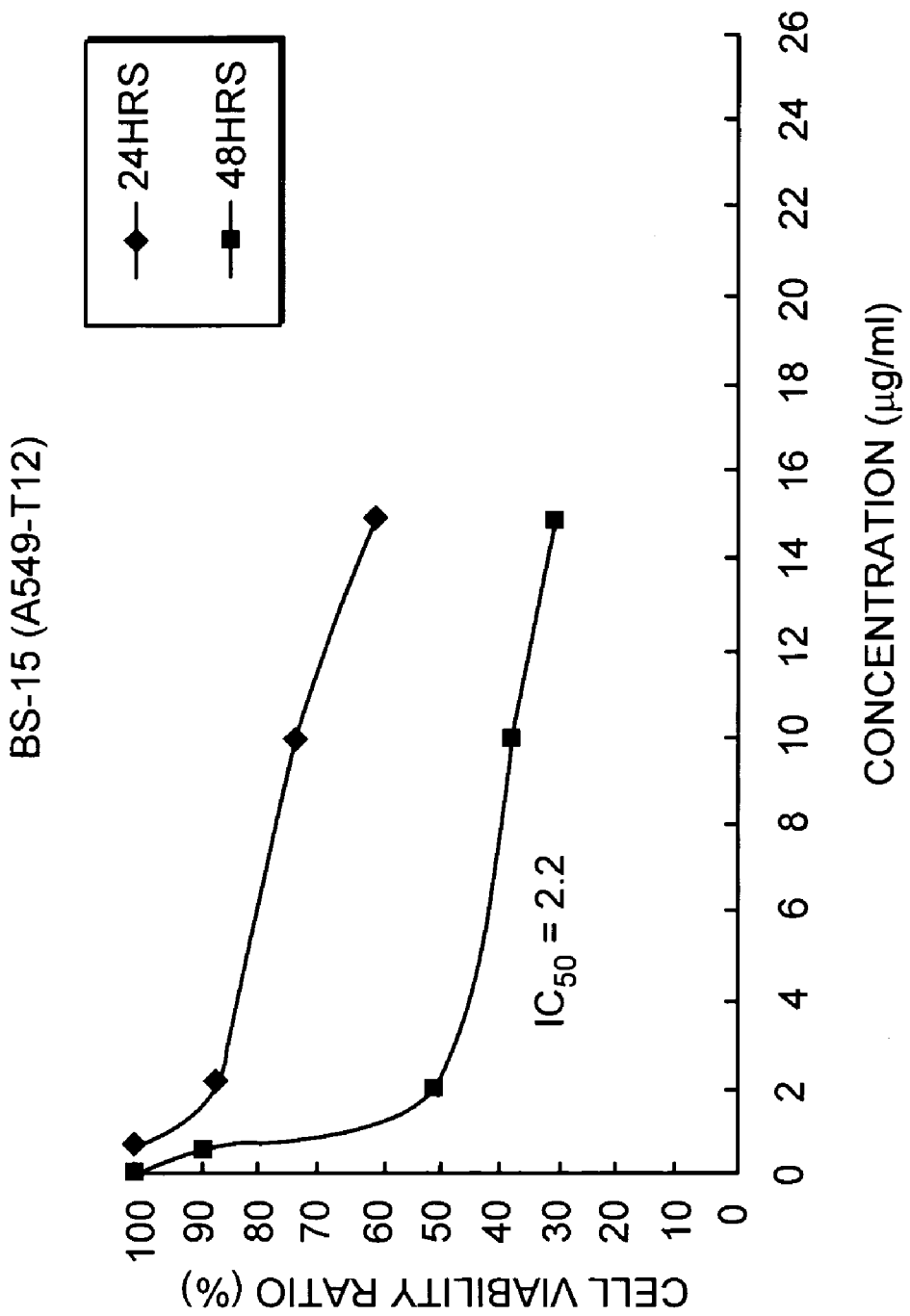
Figure 11A:
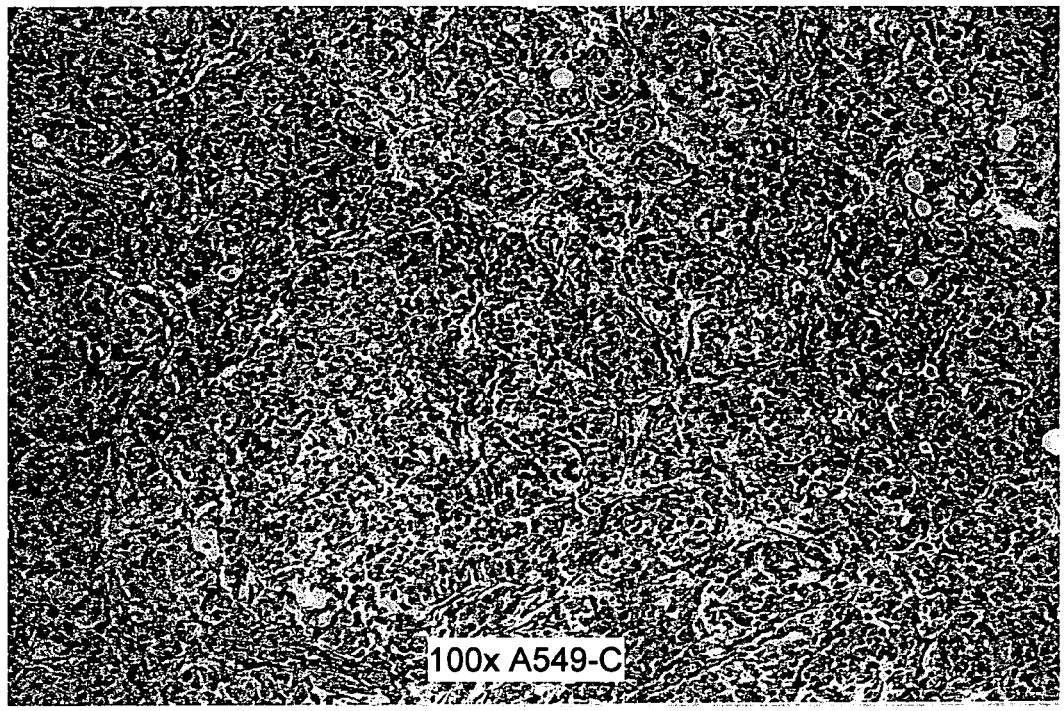
FIG. 11A is a histological section of mouse subcutaneous tumor tissue inoculated with A549 tumor cells, the section is stained with haematoxylin and eosin stain (H&E stain) and observed with a 100 times magnification.
Figure 11B:
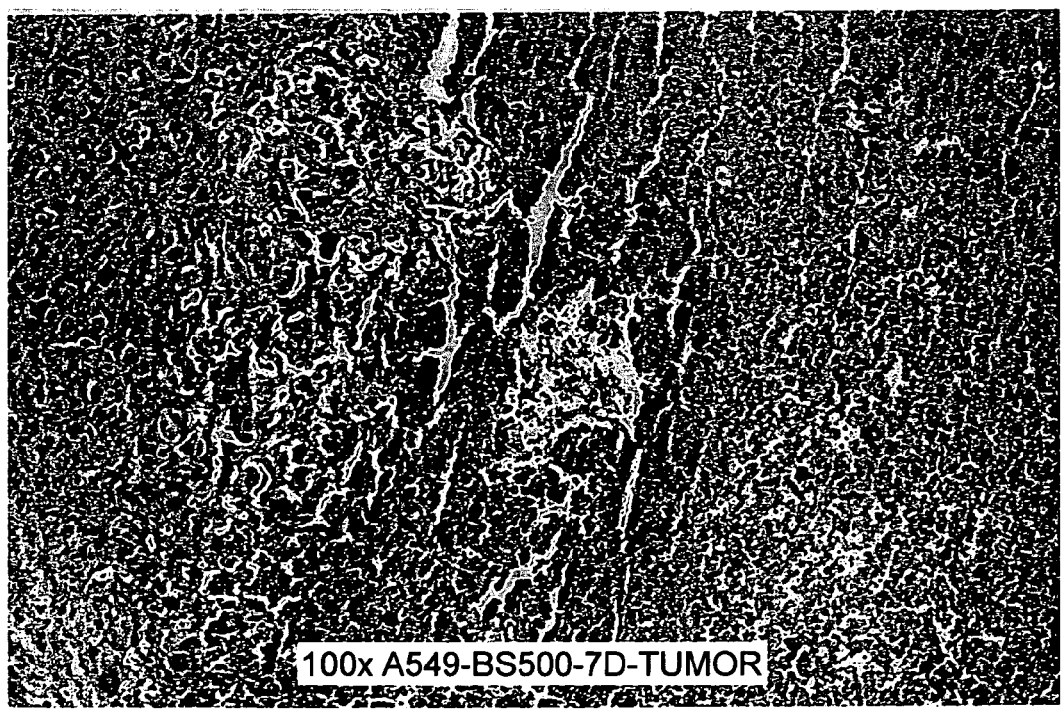
FIG. 11B is a histological section showing a large area of necrosis for tumor cells taken from the mouse subcutaneous tumor tissue inoculated with A549 tumor cells one week after intraperitoneal (I.P.) administration of 500 mg/kg of BS-AE for 5 consecutive days.

Besides, from the result FIG. 10A to 10C of cytotoxicity examination shows that after 48 hours treatment, the IC$_{50}$ of BS-AE, BS-8, and BS-15 to Taxol-resistant lung cancer cell line was shown in Table I. It demonstrates that chaihulactone, isochaihulactone, chaihulactone analogues and its derivatives are the main active materials from antineoplastic components in BS-AE crude extracts. Furthermore, a lower dose (2-4 μg/ml) of isochaihulactone is required to induce apoptosis on A549-T12 cells than that of A549 cells (8-10 μg/ml).

Sixth Embodiment

Figure 12A:
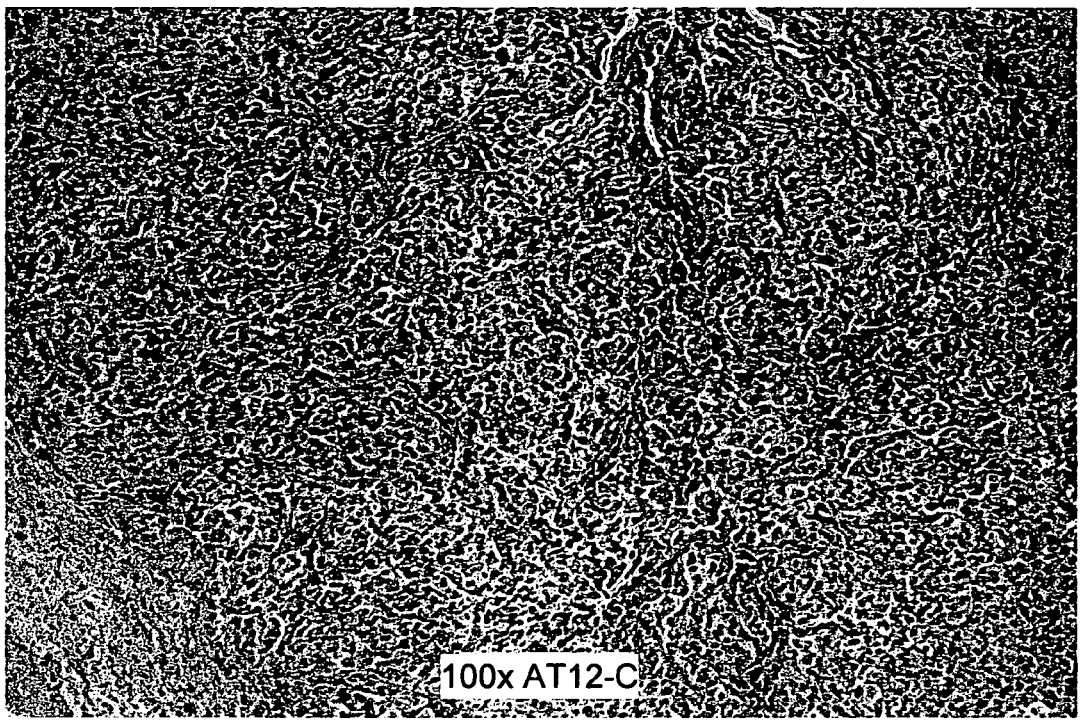
FIG. 12A is a histological section of mouse subcutaneous tissue inoculated with A549-T12 tumor cells, the section is stained with haematoxylin and eosin stain (H&E stain) and observed with a 100 times magnification.
Figure 12B:
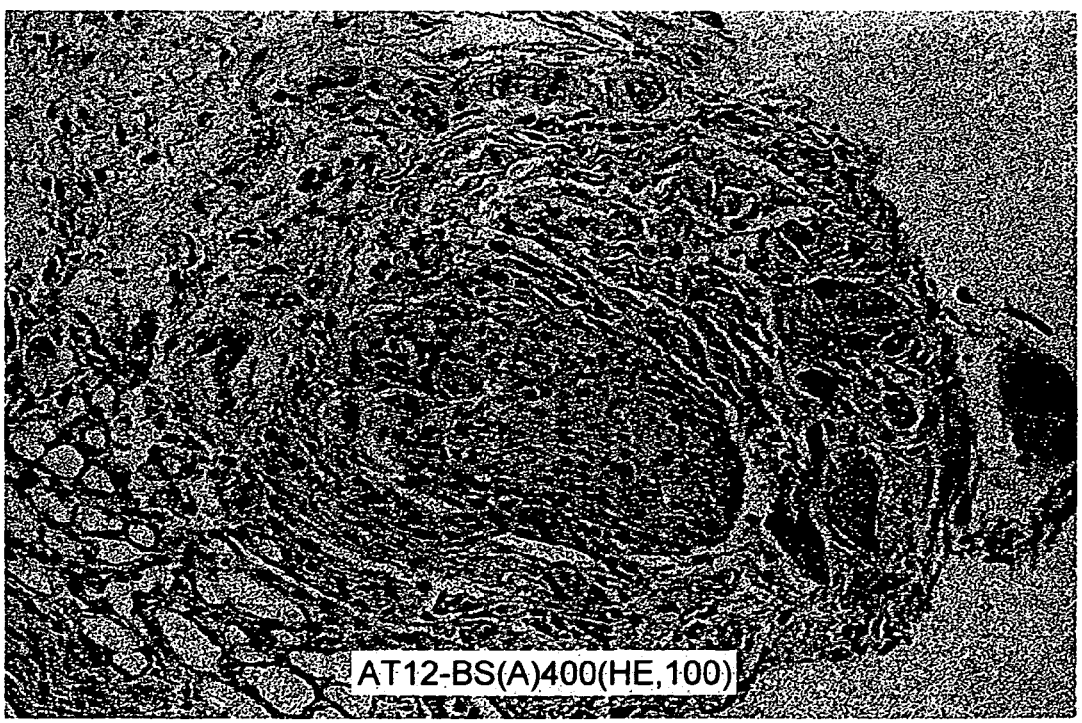
FIG. 12B is a histological section showing a large area of tissue fibrosis and only a small proportion of residual tumor cells, taken from mouse subcutaneous tumor tissue inoculated with A549-T12 tumor cells one week after I.P. administration of 400 mg/kg of BS-AE for 5 consecutive days.
Figure 13A:
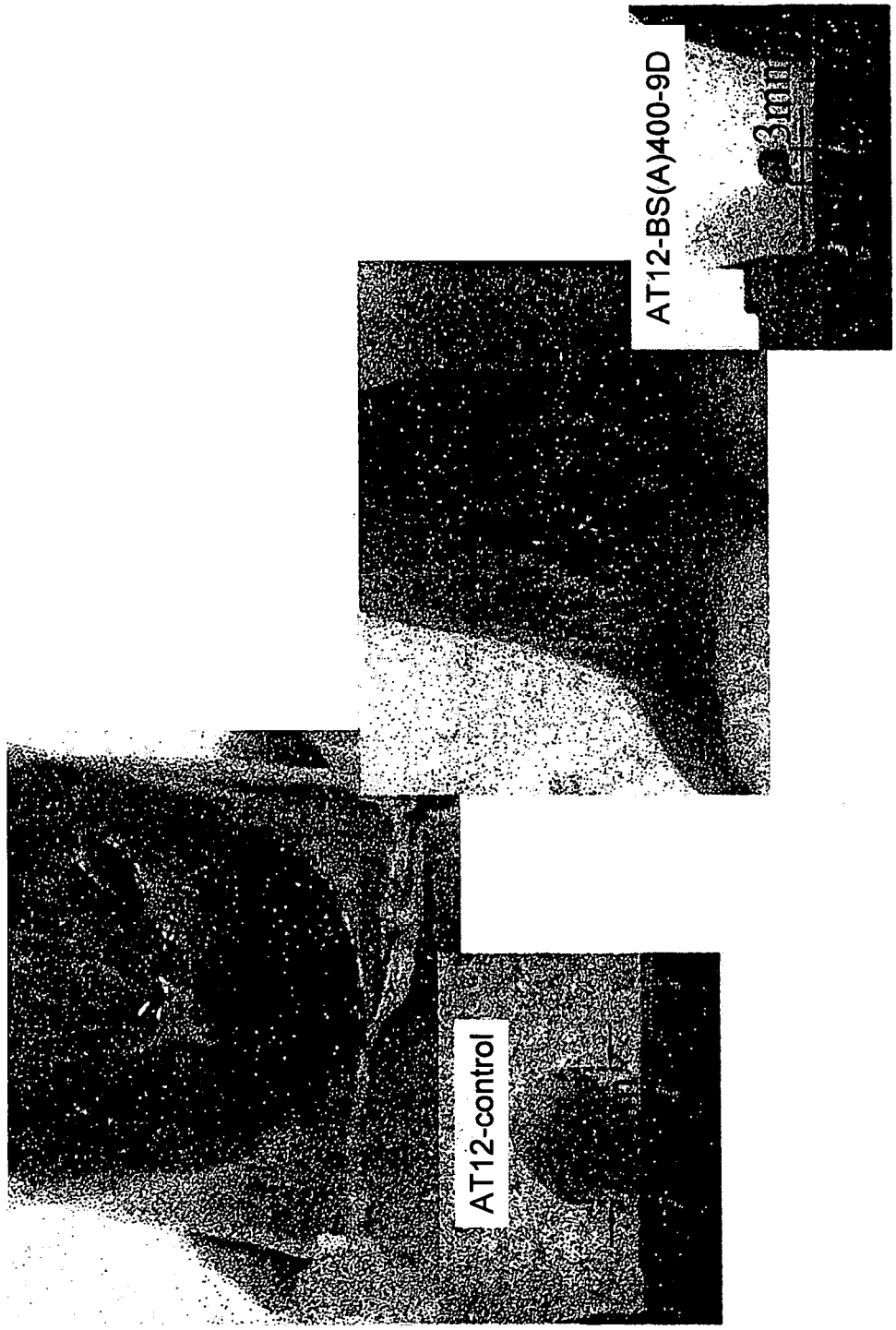
FIG. 13A are partial magnified pictures showing diameters of subcutaneous tumors taken one week after from a nude mouse inoculated with A549 tumor cells and I.P. administered with 500 mg/kg of BS-AE for 5 consecutive days.
Figure 13B:
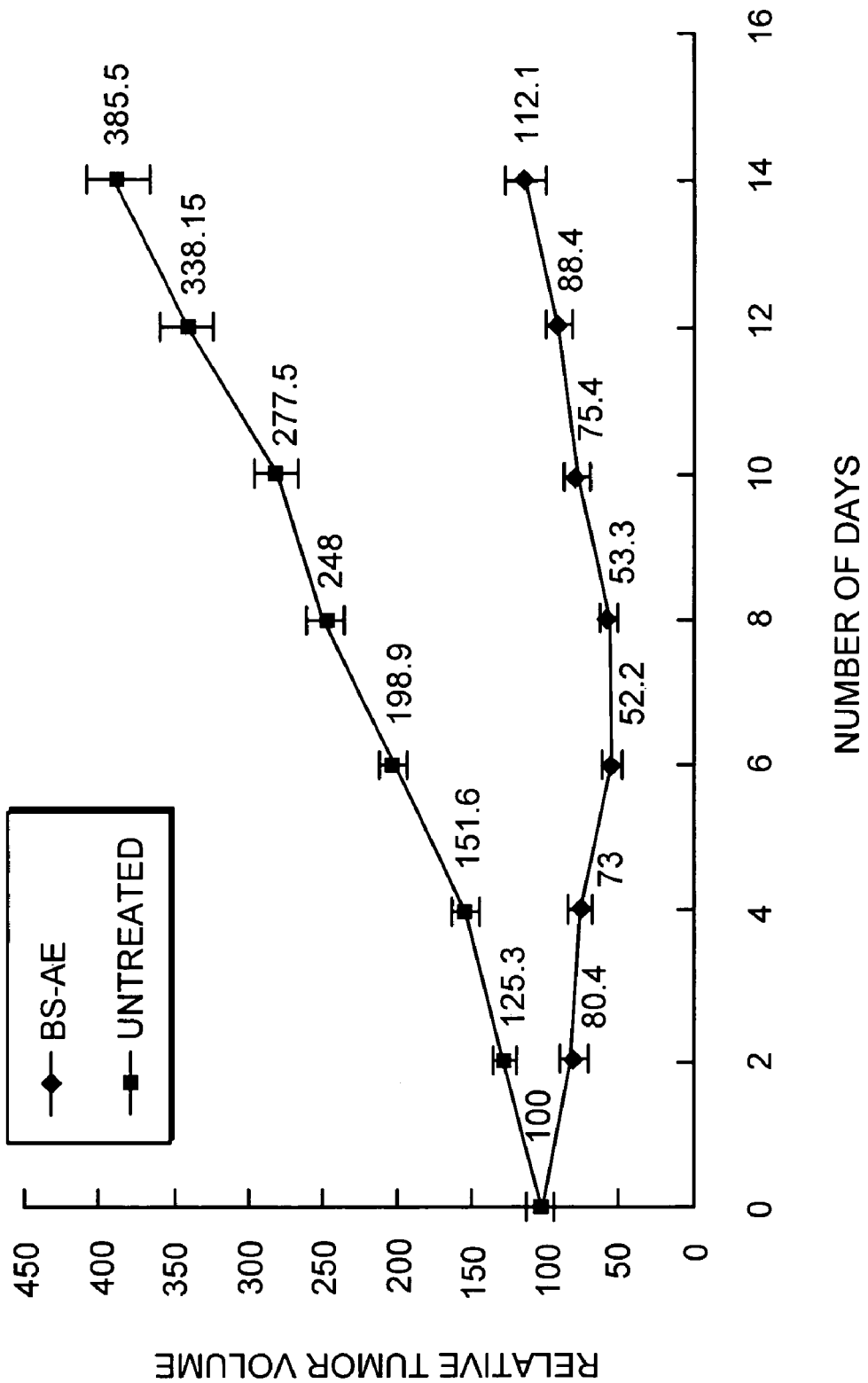
FIG. 13B is a curve showing relative volume changes of subcutaneous tumors from the mouse untreated and the mouse that is I.P. administered with 500 mg/kg of BS-AE with respect to the number of days for treatment.
Figure 14A:
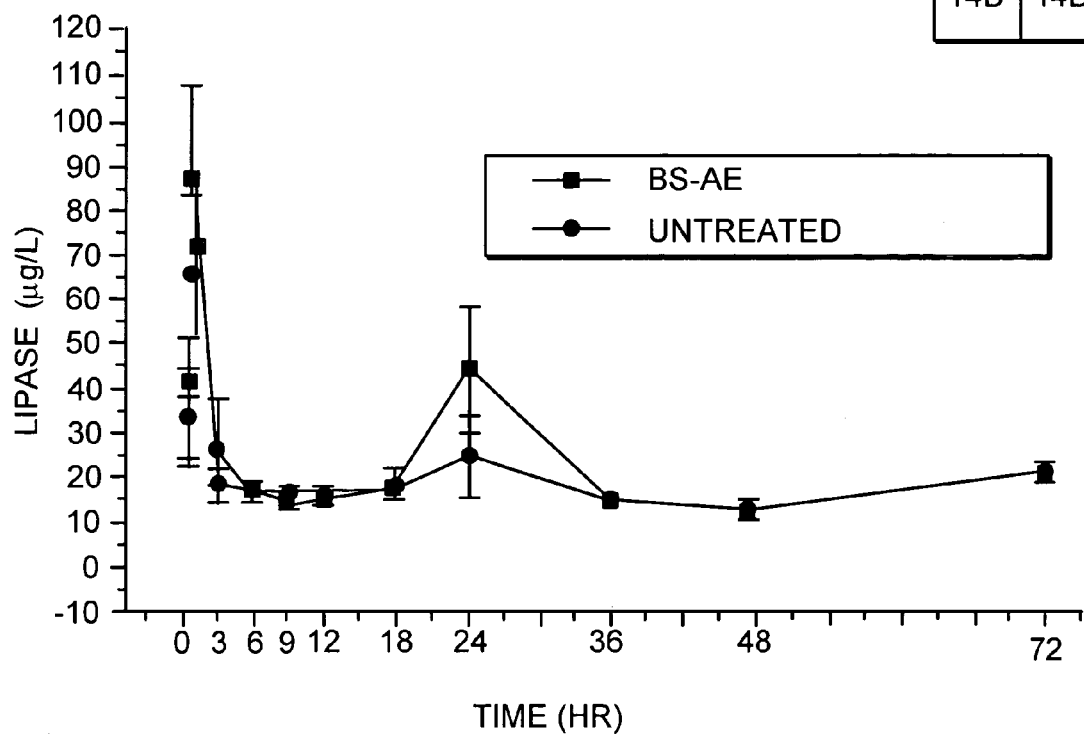
FIG. 14 includes a variety of statistical curves showing changes in indicative enzyme levels corresponding to the functionality of pancreas, liver, heart, kidney and hematopoietic systems in a conscious mouse within 72 hours after intravenous administration of 400 mg/kg of BS-AE to the mouse.
Figure 14A:
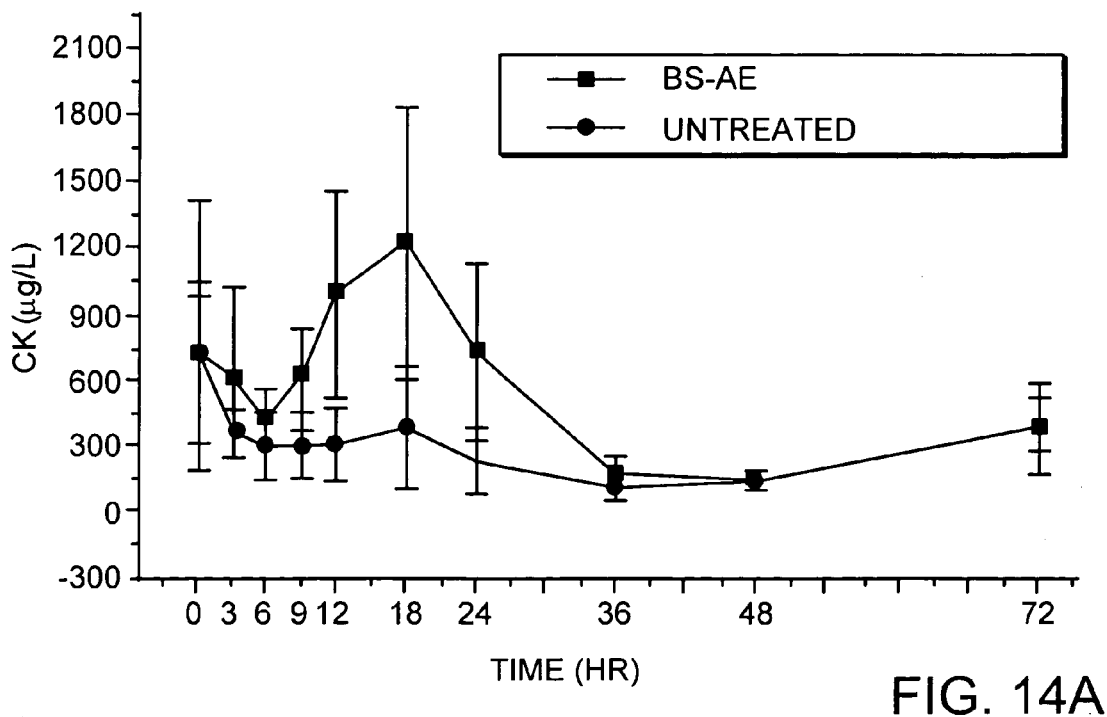
Figure 14B:
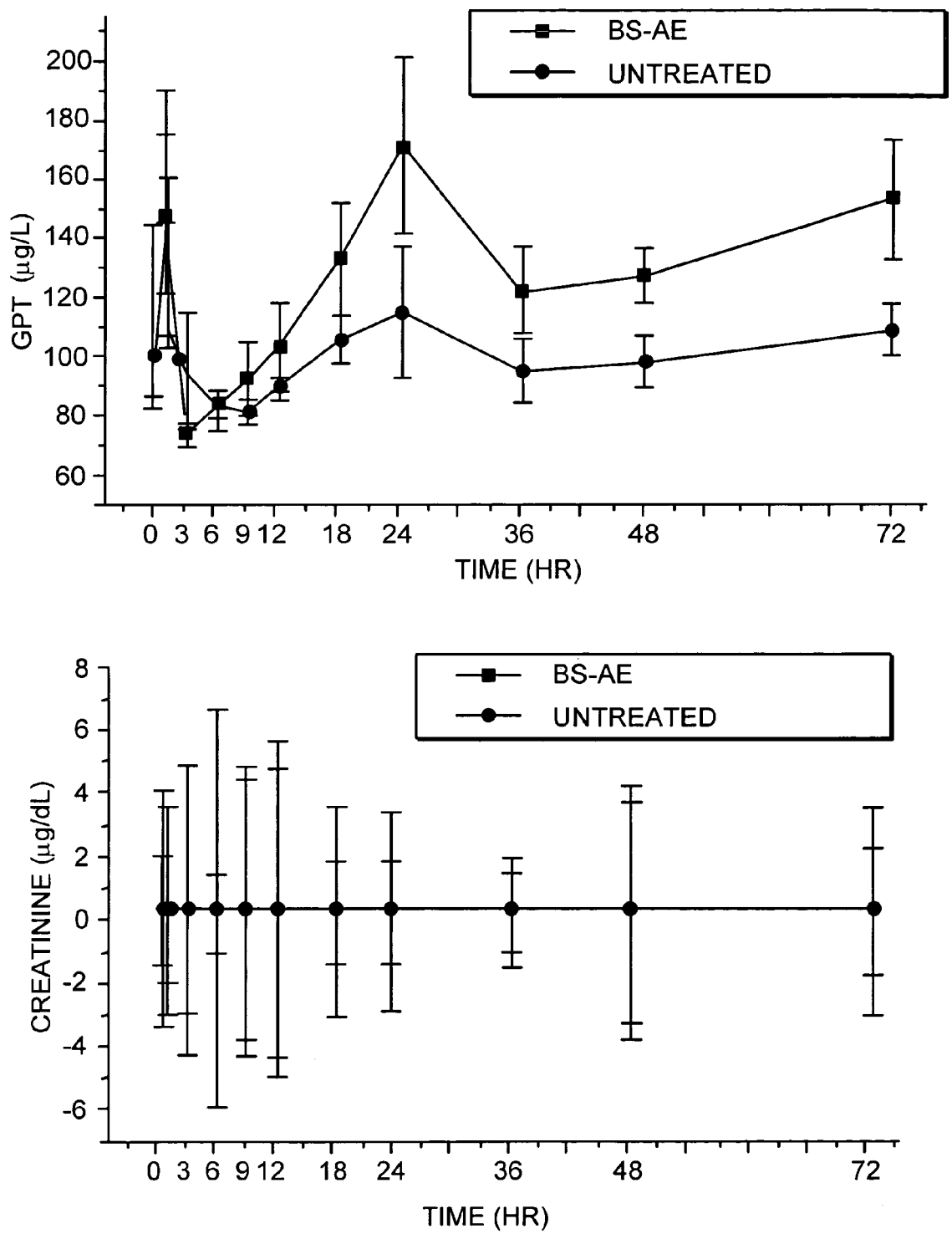
Figure 14C:
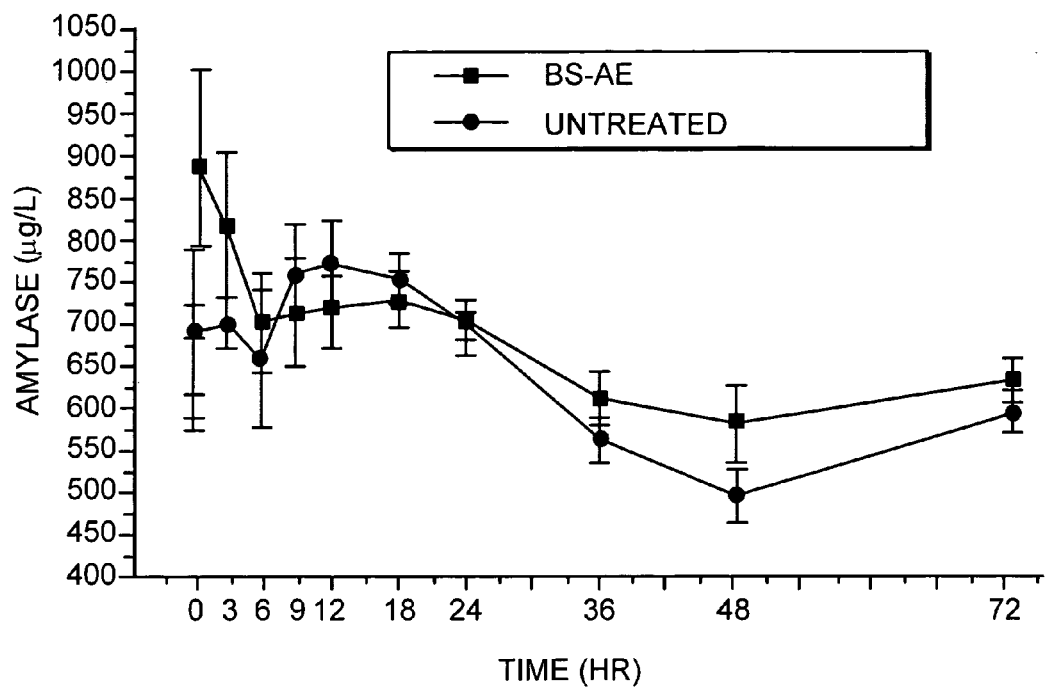
Figure 14C:
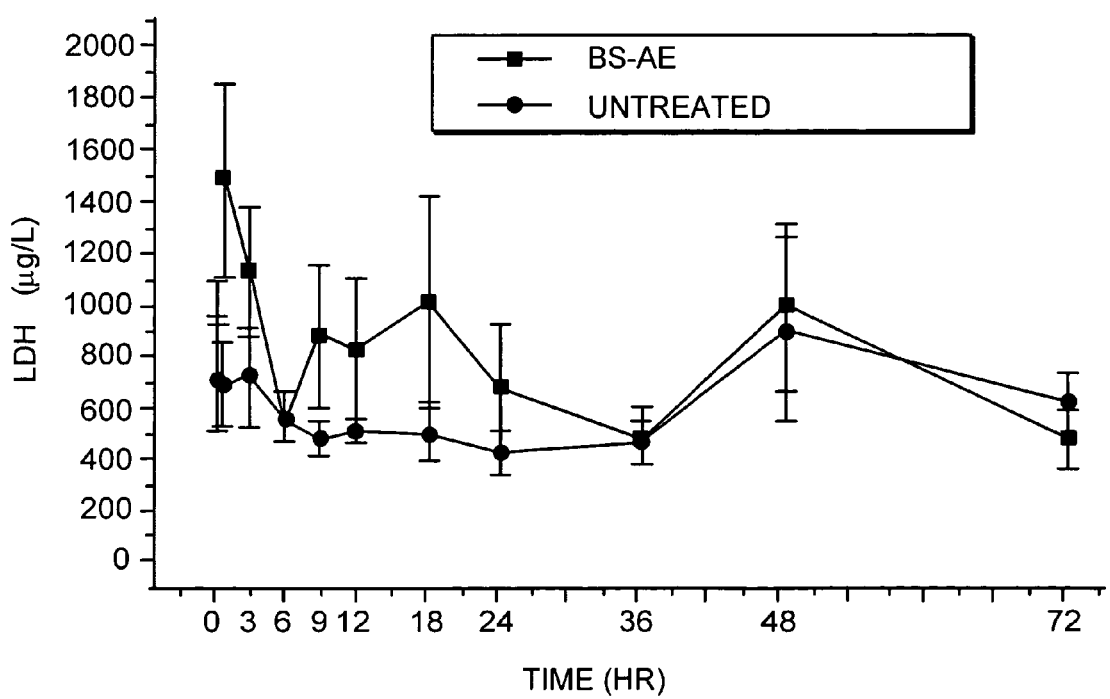
Figure 14D:
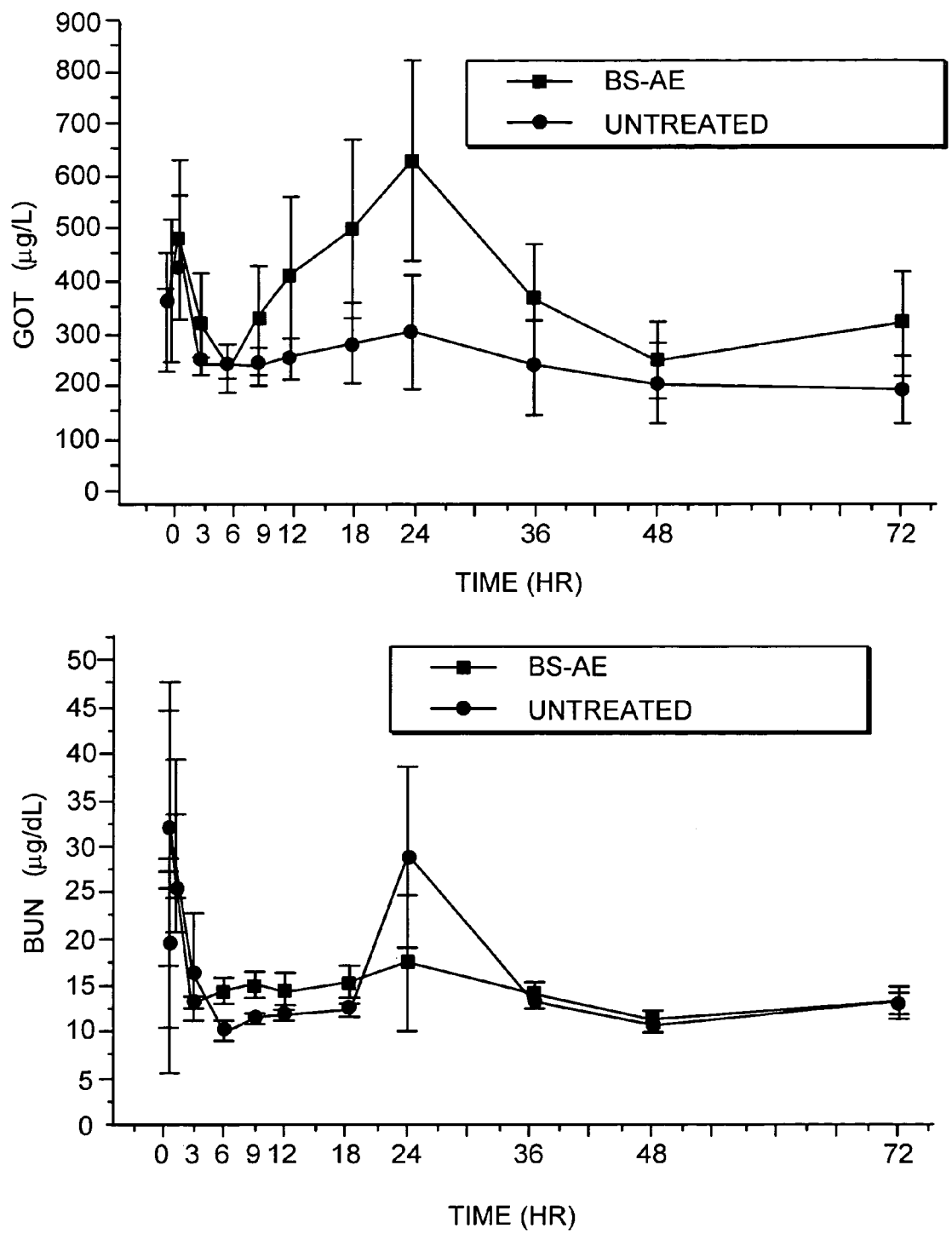

The Estimate of the Antineoplastic Effect of *Bupleurum scorzonerifolium* Extracts in Vivo Histological examinations were conducted to examine the antineoplastic effects of BS-AE on A549 cell and A549-T12 cells in vivo. FIGS. 11A, 11B, 12A, and 12B show the comparison of tumor tissue necrosis before and after the administration of BS-AE from 100× histological slide stained with haematoxylin and eosin stain (H&E stain). It is found that, as 300-500 mg/kg of BS-AE is IP administered to animals for 5 days, infiltration of lymphocytes, a large extent of tumor cell hemorrhage, and tumor cell necrosis occur. FIG. 12B shows that after BS-AE treatment, only a few tumor cells remained on the tissue. As shown in the comparison FIG. 13A, the volume of tumor from subcutaneous tumor tissue (A549 cell line) clearly decrease by 77% after 500 mg/kg of BS-AE is given. From the tumor volume shown in FIG. 13B, it was found that tumor volume was clearly decreased after the BS-AE treatment. Therefore, it can be understood from histological examination and hypodermic tissue that BS-AE has anti-tumor effect in vivo.

Seventh Embodiment

The Cytotoxicity of *Bupleurum scorzonerifolium* Extracts on Cells and Animal Models It is known from the experimental result of this invention, BS-AE have significant anti-proliferative effect on human hepatoma, lung cancer, ovarian cancer, malignant glioblastoma and colorectal carcinoma cells. From the in vivo animal study, BS-AE is proved to have anti-tumor effect in vivo. Therefore, in order to analyze the possibility of using BS-AE as current medicine, any harmful side effects associated with using BS-AE on the other normal cells or organs should be evaluated. A conscious rat is used in this invention to show the change of all enzymes in the organs of mouse after 400 μg/kg of *Bupleurum scorzonerifolium* extract is given.

Figure 15A:
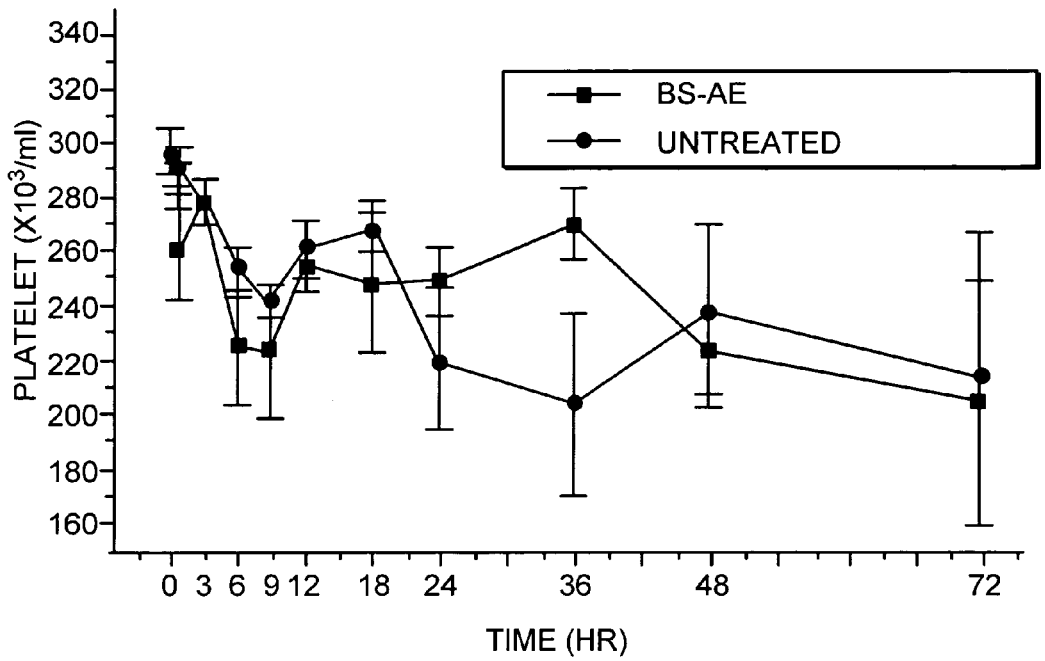
FIG. 15 includes a variety of statistical curves showing changes in platelets, white blood cells, and lymphocytes in the conscious mouse within 72 hours after intravenous administration of 400 mg/kg of BS-AE to the mouse.
Figure 15A:
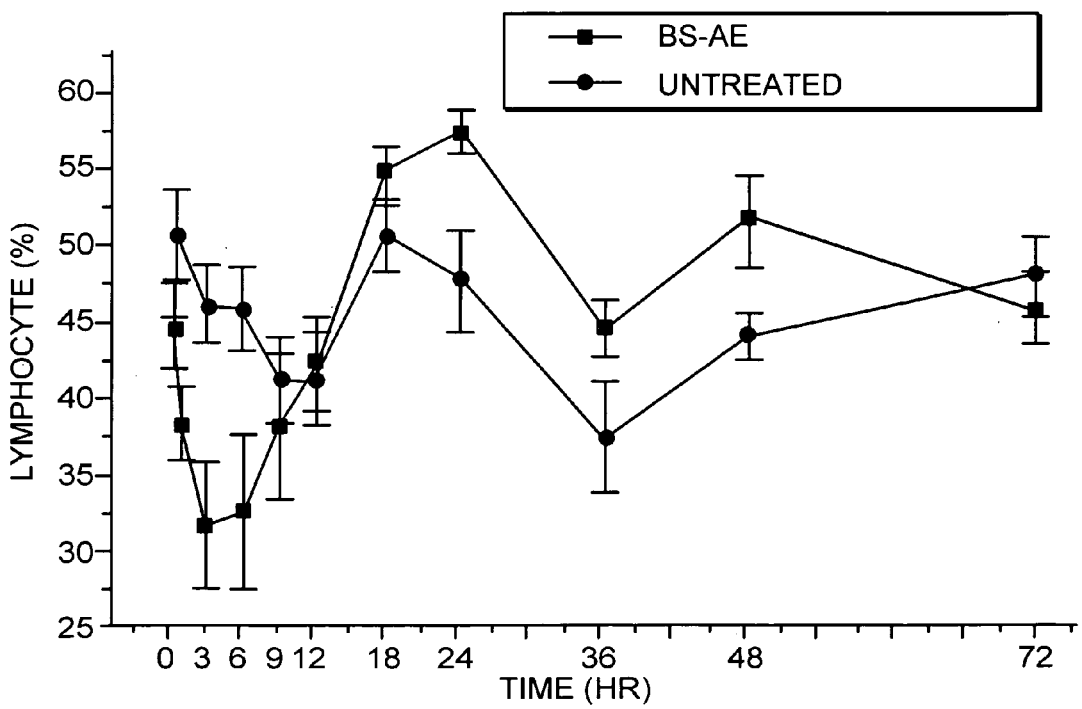
Figure 15B:
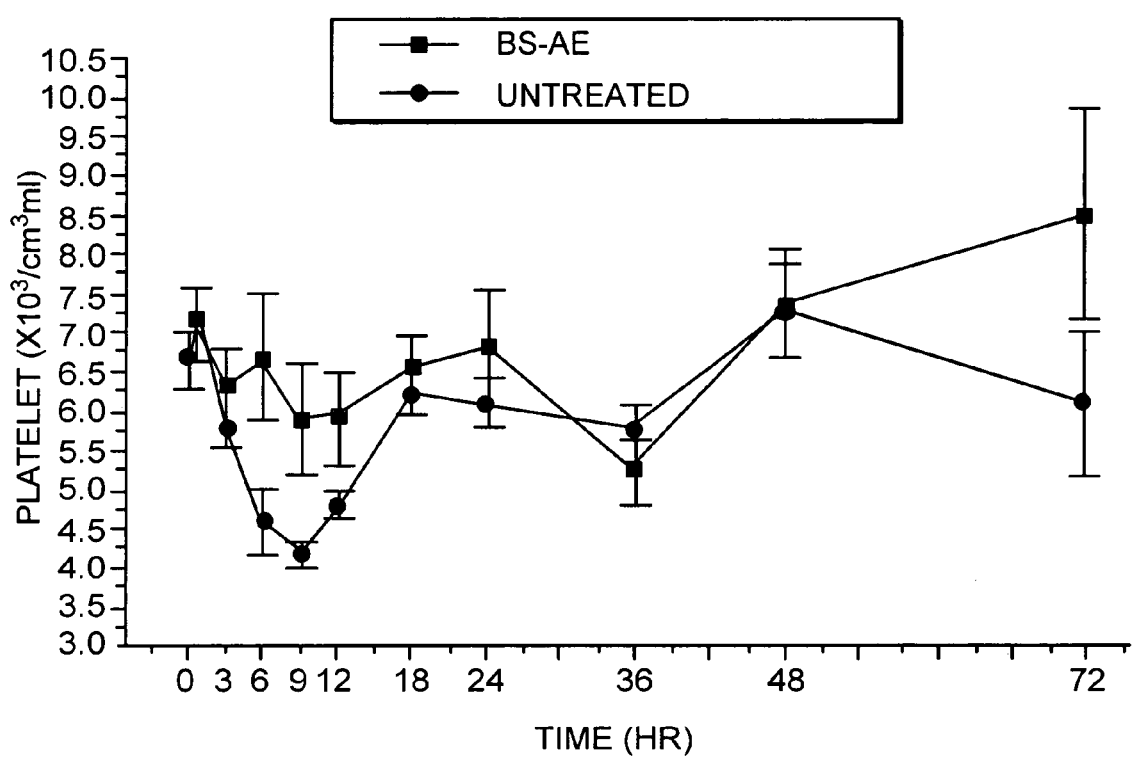
Figure 16A:
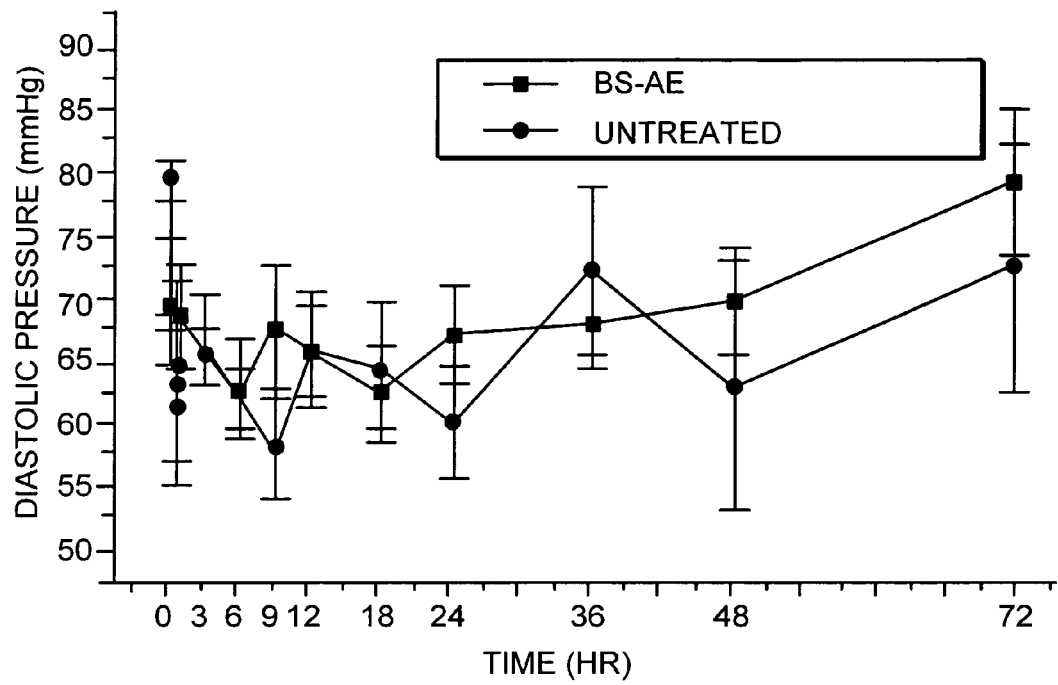
FIG. 16 includes a variety of statistical curves showing changes in cardiac pulse, diastolic pressure, systolic pressure, and average blood pressure in the conscious mouse within 72 hours after intravenous administration of 400 mg/kg of BS-AE to the mouse.
Figure 16A:
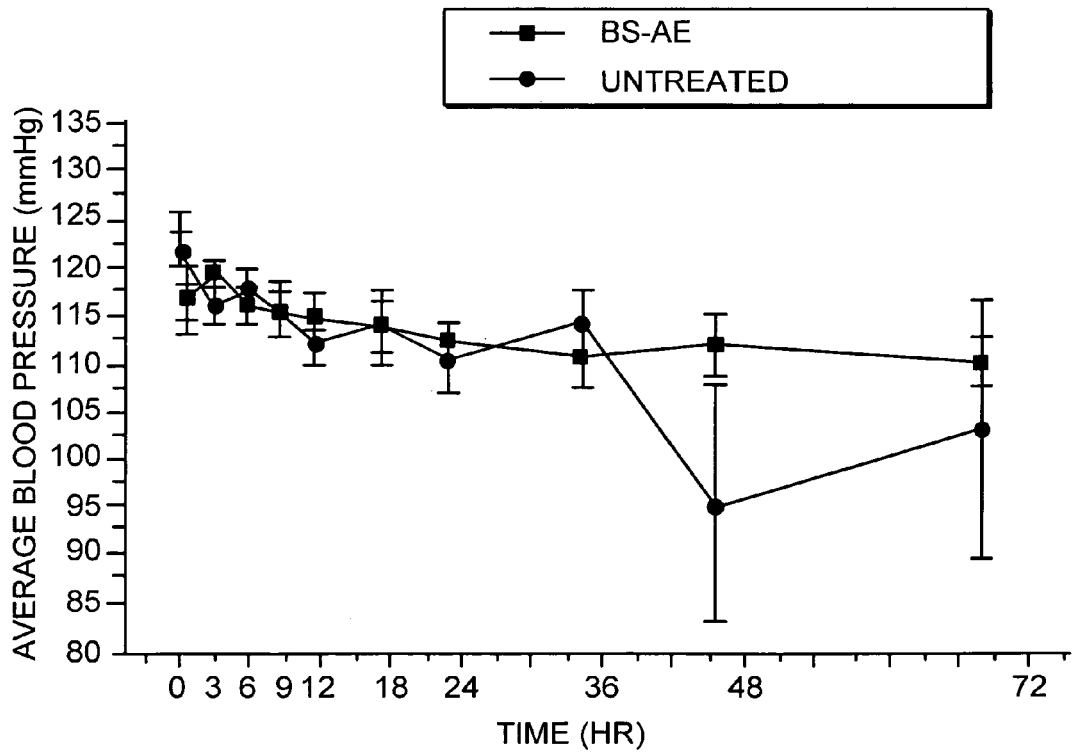
Figure 16B:
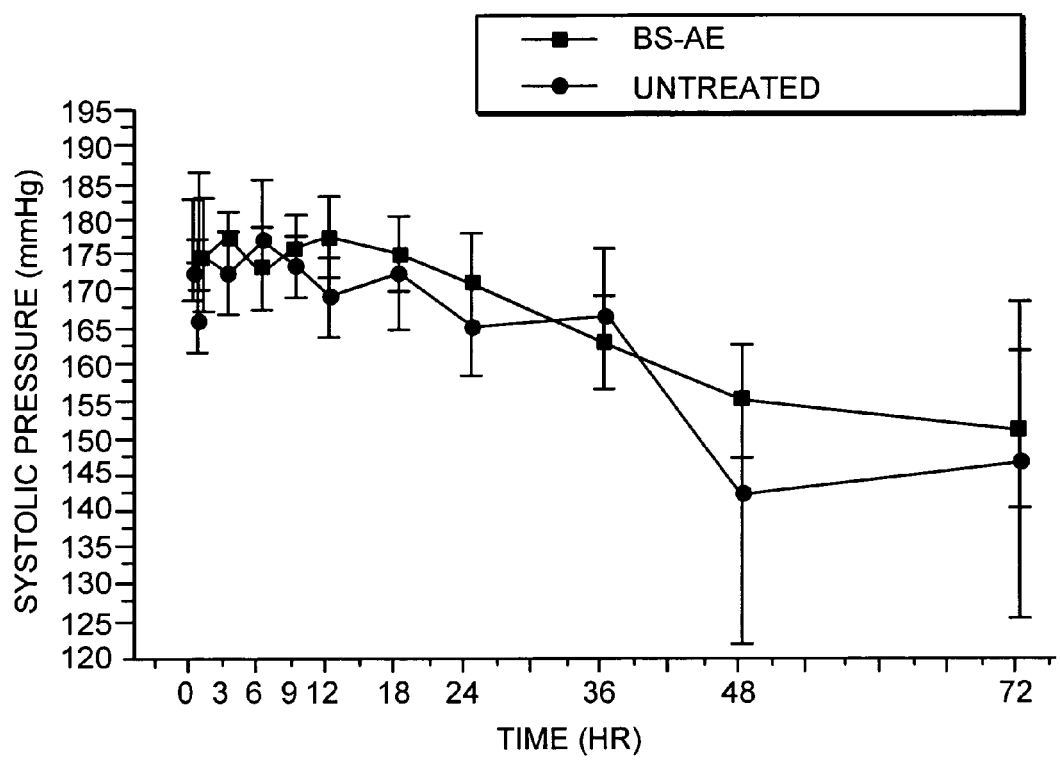
Figure 16B:
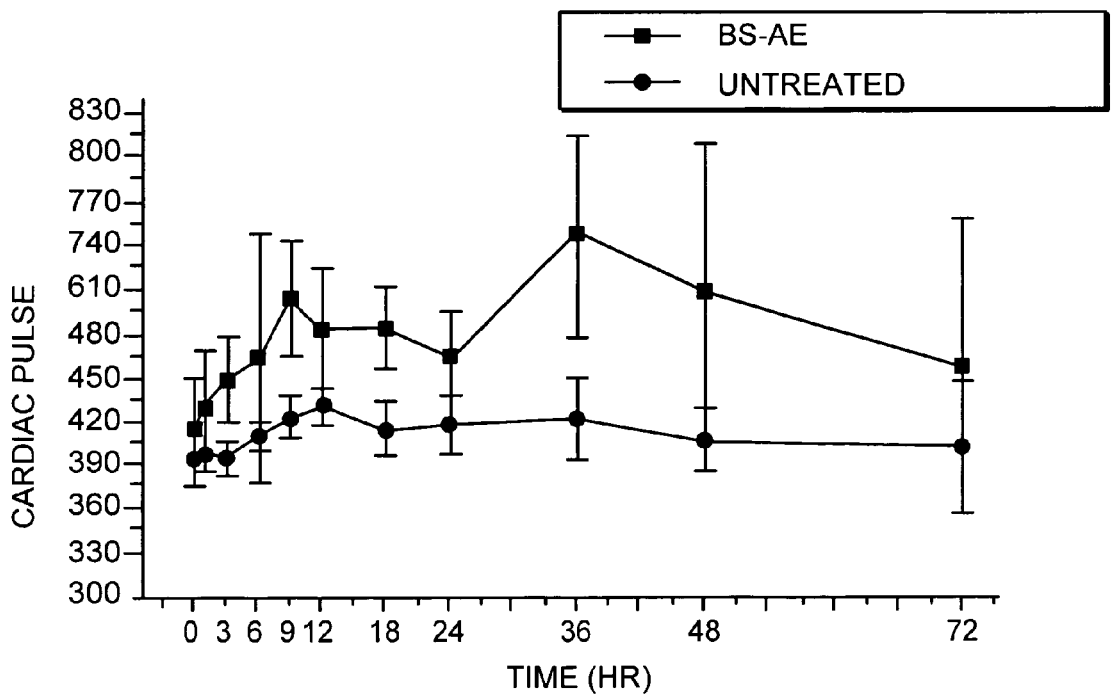
Figure 17:
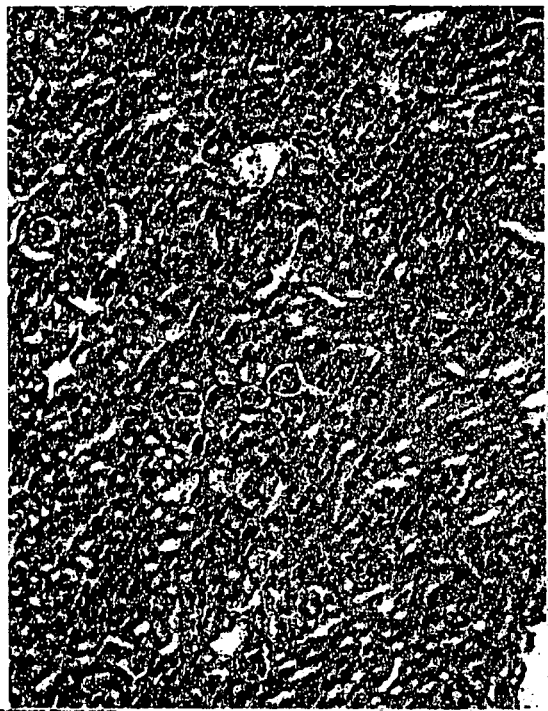
FIG. 17 includes histological sections illustrating liver cells and kidney cells of the conscious mouse after 300 mg/kg of BS-AE is I.P. administrated to the mouse for 5 consecutive days.
Figure 17:
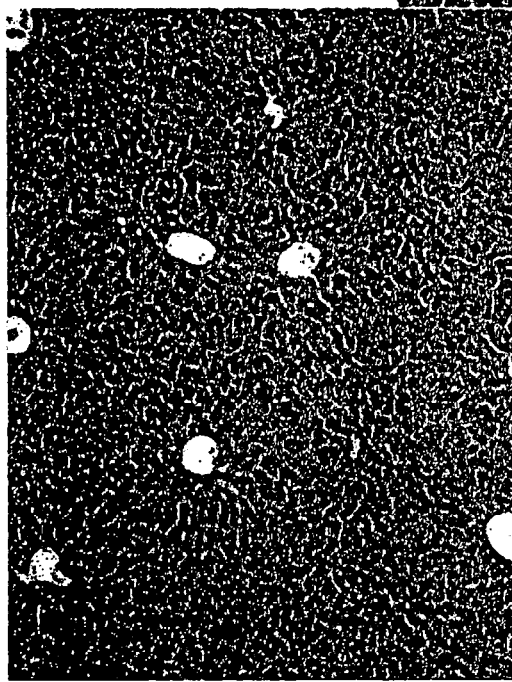

As shown in FIG. 14 and FIG. 15, after 72 hours of giving 400 μg/kg of BS-AE intravenously to the conscious rat, there are no difference in the levels of Lipase, Amylase, glutamic oxaloacetic transaminase (GOT), glutamic pyruvic transaminase (GPT), Lactate Dehydrogenase (LDH), Creatinine Kinase (CK), Creatinine, Blood Urea Nitrogen (BUN), pulse, diastolic pressure, systolic pressure, platelets and white blood cells as compare to those of the control group without treatment. This indicates the intravenous (I.V.) administration has no significant toxic effects for digestive, circulation, metabolic systems, haemopoietic mechanism and germ cells. The liver and kidney histological examinations in FIG. 15 prove that the normal cells of liver and kidney are not destroyed after intraperitoneal (I.P.) administration of 300 μg/kg of BS-AE for 5 consecutive days. Therefore, from all the results obtained previously, BS-AE administered in vivo has no effect on the normal cells or organ functions at the therapeutic dosage. Thus, BS-AE could provide a new antineoplastic source to the cancer patients and those patients who developed resistance to Taxol.

Eighth Embodiment

The Synergistic Effect of *Bupleurum scorzonerifolium* Extracts on Other Anti-Tumor Drugs According to the results from previous embodiment, it is understood that *Bupleurum scorzonerifolium* extracts, particularly BS-AE, isochaihulactone, and chaihulcatone are effective in inducing apoptosis to Taxol-resistant cells, suggesting synergistic effect of *Bupleurum scorzonerifolium* extracts on Taxol. In recent clinical treatment, two types of anti-tumor drugs, such as Cisplatin, Caroplatin, Bleomycin, Adriamycin, and Vinblastin are usually used in conjunction to improve survival rate of tumor patients at later stage and alleviate side effect of the drug. Therefore, the synergistic effect of *Bupleurum scorzonerifolium* extracts on the anti-tumor drug is estimated by comparing inhibitory effect on the growth of the tumor using either single anti-tumor drug or cocktail of *Bupleurum scorzonerifolium* extracts and the anti-tumor drugs.

Figure 18:
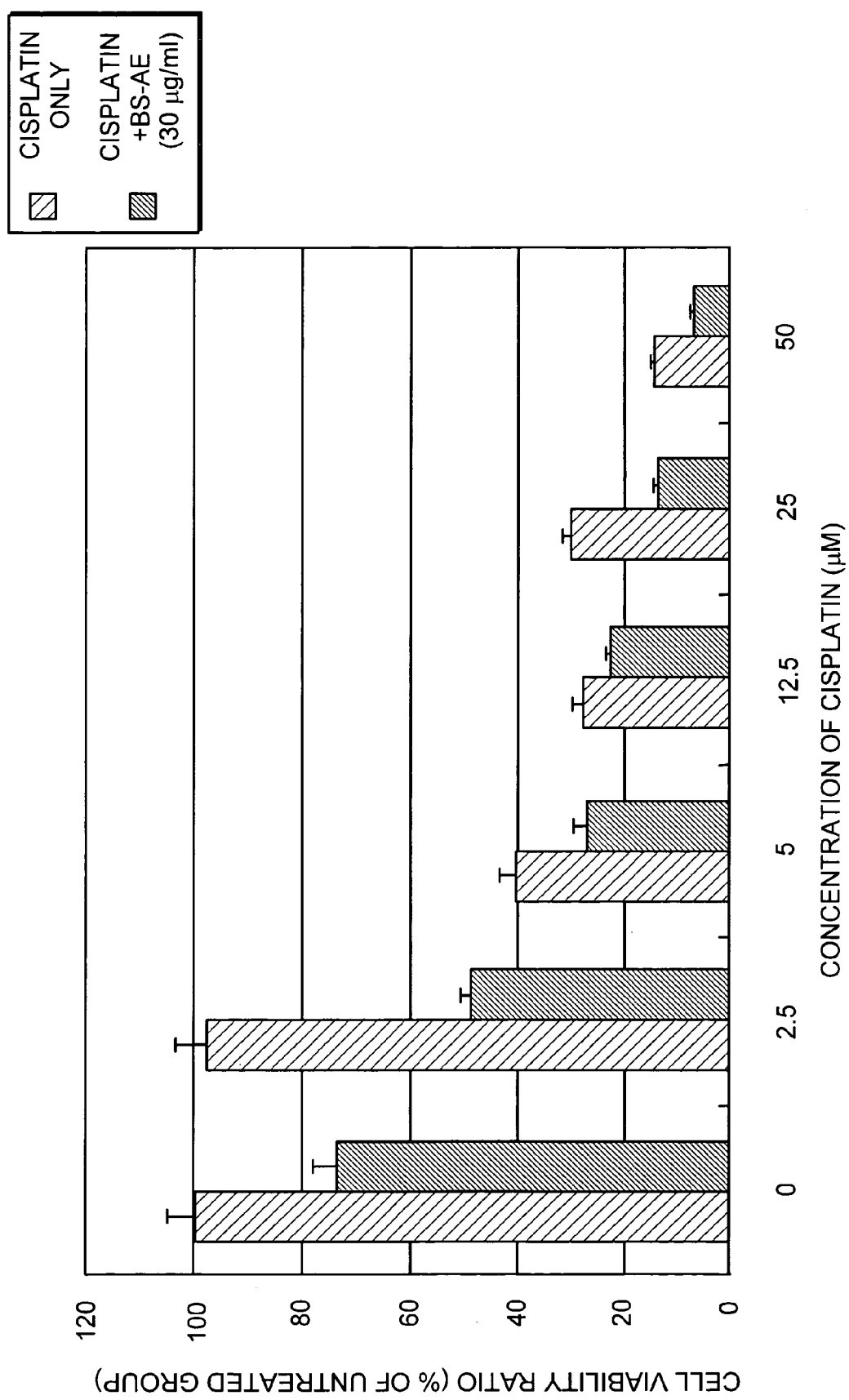
FIG. 18 is a bar chart showing cell viability ratio (in percentage of untreated group) for A549 cells either treated only with Cisplatin at different concentrations or treated with Cisplatin and 30 µg/ml of BS-AE.

The inhibitory effect on the growth of tumor cells is studied using A549 cells treated either with Cisplatin or Cisplatin and co-treatment of 30 μg/ml of BS-AE. As shown in FIG. 18, the cell viability ratio is significantly reduced when the cells were both treated with Cisplatin and BS-AE, as compared to the cell viability ratio when the cells were treated with Cisplatin alone. In other words, the same tumor growth inhibition can be achieved with less amount of anti-tumor drug administered when the anti-tumor drug is used in conjunction with BS-AE. Therefore, less cytotoxicity effect and side effect of the drug may be produced to affect the tumor patients receiving anti-tumor medication, while higher efficacy of anti-tumor treatment is achieved via synergistic effect of BS-AE on the anti-tumor drug.

Ninth Embodiment

Down-Regulatory Effect of *Bupleurum scorzonerifolium* Extracts on Telomerase Activity The tumor inhibition effect in vivo is further measured to estimate the possibility of *Bupleurum scorzonerifolium* extracts as a new source of drug developement. A telomerase repeat amplification protocol (TRAP) assay utilizing radioactive $\gamma\text{-}^{32}\text{p-ATP}$ is conducted to test telomerase activity of tumor after *Bupleurum scorzonerifolium* extracts are administered in the living animal inoculated with tumor cells, so as to determine whether BS-AE and isochaihulactone have a high specific cytotoxicity for the tumor cells.

Figure 19:
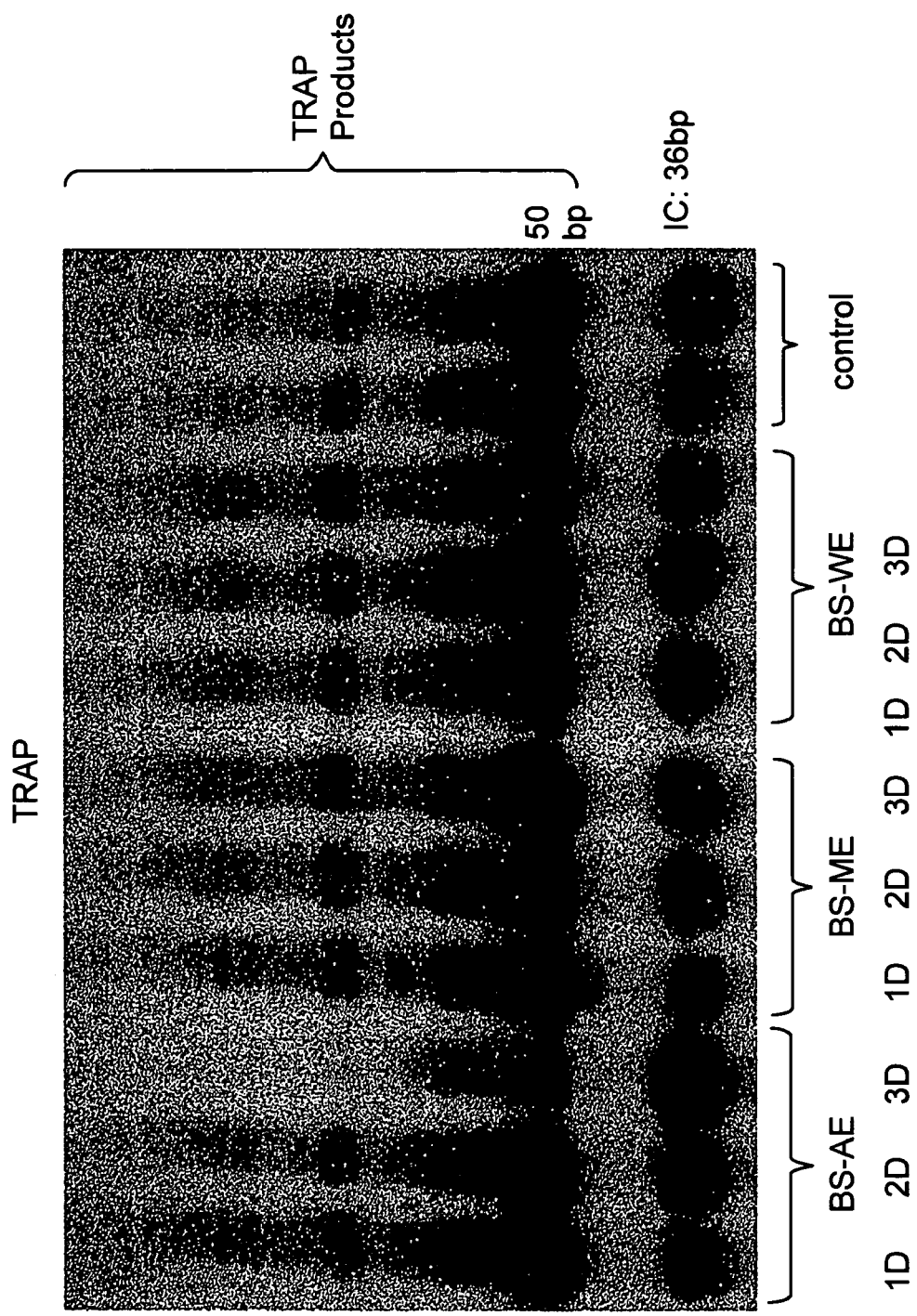
FIG. 19 is a TRAP assay analysis result showing telomerase activity of the A549 cells either treated with AZT (control), BS-AE, BS-ME, or BS-WE for 1 day (1 D), 2 days (2 D), and 3 days (3 D)

Referring to FIG. 19, the telomerase activity of the tumor cell was significantly reduced when the tumor cells A549 were treated with BS-AE. As it is evident from the current research that telomerase activity is regulated by hTERT, an anti-HIV agent, AZT that acts to down regulate expression of the hTERT gene is administered to the tumor cells A549. The down-regulatory effect of AZT is then compared with *Bupleurum scorzonerifolium* extracts. From FIG. 19, it is found *Bupleurum scorzonerifolium* extracts display a better inhibitory effect on the telomerase activity of the tumor cells than AZT, suggesting that *Bupleurum scorzonerifolium* extracts produce a stronger down-regulatory effect on expression of the hTERT gene than AZT. The down regulatory effect of *Bupleurum scorzonerifolium* extracts was further confirmed by results shown in FIG. 20, where extracts from several different Chinese herbs, such as were also included to compare with *Bupleurum scorzonerifolium* extracts for their roles in regulating expression of hTERT gene. As evident in FIG. 20, the expression of full length or spliced variant β of hTERT is suppressed following treatment with BS-AE, while the tumor cells treated with other extracts are not inhibited in expressing hTERT. Thus, it is very likely that *Bupleurum scorzonerifolium* extracts, particularly the acetone extract thereof further provides anti-HIV effect other than AZT and other anti-HIV agents that act to inhibit telomerase activity.

In conclusion, the antineoplastic components extracted from *Bupleurum scorzonerifolium* comprises *Bupleurum scorzonerifolium* acetone crude extract containing Y-butyrolactone centred heterocyclic compounds forming Z or E configuration, *Bupleurum scorzonerifolium* novel compounds, "chaihulactone analogues or derivatives," extracted from the acetone crude extract and other pharmacologically compatible salts, esters, ketones and their analogues and derivatives extracted from *Bupleurum scorzonerifolium* that have potential to be used in the treatment of hepatoma, ovarian cancer, lung cancer, malignant glioblastoma or colorectal carcinoma.

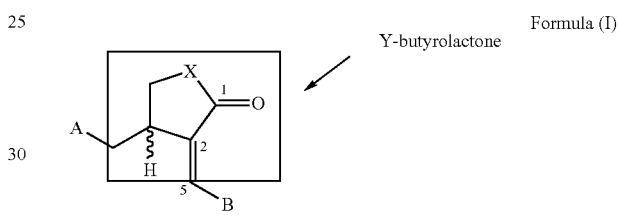

where the heterocyclic compound may have a 3R or 3S configuration, X can be N, O, S, or Se, and A, B can be selected from the following substituents:

where R1, R2, R3, R4, R5 can be selected from a hydrogen atom, a halogen atom, a hydroxyl group, a sulfoxyl group, an amino group, a methoxyl group, and a nitro group.

In accordance with the foregoing preferred embodiments of the invention, it is realised that the acetone crude extract being extracted from *Bupleurum scorzonerifolium* has more significant antineoplastic effects. Moreover, after applying BS-AE and isochaihulactone to both tumor cells and Taxol-resistant tumor cells, they all show significant inhibition effects. And BS-AE could reduce telomerase activity, suppress cell proliferation, enhance cell apoptosis, and have in vivo anti tumor effect, while there is no significant toxicity to body systems such as digestive, circulation, metabolic systems, haemopoietic mechanism and genital system.

In terms of cell control mechanism, BS-AE and isochaihulactone act as a microtubule stabilizing agent, which promotes polymerization of β-tubulin inhibiting cancer cell mitosis and leading to cell death. The mechanism leading to cell death is similar to that of Taxol for keeping the tumor cells arrested at G2/M stage of the cell cycle and inhibiting further cell proliferation.

The invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A method for preparing an extract from *Bupleurum scorzonerifolium*, wherein the extract comprises antineoplastic components, comprising the steps of:
    dissolving *Bupleurum scorzonerifolium* powder using an acetone solution to obtain an acetone extract and residues;
    dissolving the acetone extract in a protic solvent solution and extracting the protic solvent solution with a nonpolar organic solvent, to obtain a nonpolar organic solvent extract and a protic solvent portion; and
    dissolving the protic solvent portion in an aqueous solvent and extracting with a polar organic solvent to obtain a polar organic solvent extract comprising the antineoplastic components therein.

2. The method of claim 1, wherein the protic solvent solution is 95% methanol/5% water.

3. The method of claim 1, wherein the aqueous solvent is water.

4. The method of claim 1, wherein the nonpolar organic solvent is hexane.

5. The method of claim 1, wherein the polar organic solvent is chloroform.

6. The method of claim 1, wherein the antineoplastic components have anti-tumor effects on hepatoma.

7. The method of claim 1, wherein the antineoplastic components have anti-tumor effects on ovarian cancer.

8. The method of claim 1, wherein the antineoplastic components have anti-tumor effects ons malignant glioblastoma.

9. The method of claim 1, wherein the antineoplastic components have anti-tumor effects on lung cancer.

10. The method of claim 1, wherein the antineoplastic components have anti-tumor effects oncolorectal cancer.

11. The method of claim 1, wherein the antineoplastic components have anti-tumor effects on tumors which are resistant to a taxane-type anticancer agent.

12. The method of claim 11, wherein the taxane-type anticancer agent is Paclitaxel.

13. The method of claim 1, wherein the antineoplastic components comprise a compound having the following formula:

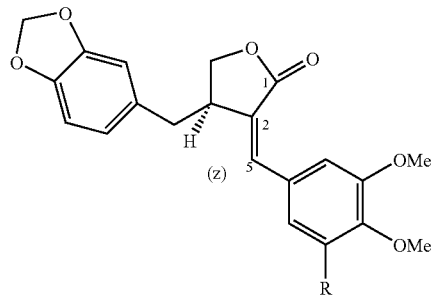

where R represents a hydrogen atom, a methoxyl group, or an aromatic group.

14. The method of claim 1, wherein the antineoplastic components arrest a G2/M stage of a cell cycle.

15. The method of claim 1, wherein the antineoplastic components stabilize a microtubule.

16. The method of claim 1, wherein the antineoplastic components down-regulate human telomerase reverse transcriptase (hTERT) gene.

17. The method of claim 16, wherein the antineoplastic components down regulate hTERT gene in human immunodeficiency virus (HIV).

18. The method of claim 1, wherein the antineoplastic components inhibit telomerase activity.

19. The method of claim 18, wherein the antineoplastic components inhibit telomerase activity in HIV.

* * * * *